United States Patent
Buijsman et al.

(10) Patent No.: US 7,576,071 B2
(45) Date of Patent: Aug. 18, 2009

(54) ANTITHROMBOTIC COMPOUND

(75) Inventors: Rogier Christian Buijsman, Oss (NL); Martin De Kort, Oss (NL); Dirk Gerrit Meuleman, Oss (NL); Constant Van Boeckel, Oss (NL)

(73) Assignee: sanofi-aventis, Paris (FR)

( * ) Notice: Subject to any disclaimer, the term of this patent is extended or adjusted under 35 U.S.C. 154(b) by 344 days.

(21) Appl. No.: 11/468,988

(22) Filed: Aug. 31, 2006

(65) Prior Publication Data

US 2007/0293442 A1    Dec. 20, 2007

Related U.S. Application Data

(63) Continuation of application No. PCT/EP2005/002881, filed on Mar. 3, 2005.

(30) Foreign Application Priority Data

Mar. 5, 2004  (EP) .................. 04005343

(51) Int. Cl.
*A61K 38/14*  (2006.01)
*A61K 31/737*  (2006.01)
*C07G 3/00*  (2006.01)
*C07H 15/18*  (2006.01)

(52) U.S. Cl. .............. 514/54; 514/8; 536/4.1; 536/123; 536/123.1

(58) Field of Classification Search .............. None
See application file for complete search history.

(56) References Cited

U.S. PATENT DOCUMENTS

| 6,022,854 A | | 2/2000 | Shuman |
| 6,136,794 A | * | 10/2000 | Cook et al. ............ 514/56 |
| 6,384,021 B1 | | 5/2002 | Mardigulan |
| 6,486,129 B1 | | 11/2002 | Tromp et al. |

FOREIGN PATENT DOCUMENTS

WO    WO01/42262    *  6/2001

OTHER PUBLICATIONS

Merriam-Webster's Collegiate Dictionary, Tenth Edition, published 1998 by Merriam-Webster, Incorporated, p. 924.*
2006 Chemical Abstracts Catalog, published 2006 by Chemical Abstracts Srevice, p. 52.*
Adang Anton E P et al., A New Generation of Orally Active Antithrombotics: Comparing Strategies in the GPIIb/IIIa, Thrombin and Factor Xa Areas, Drugs of the Future 2000; vol. 25(4); pp. 369-383.
Uzan, A., Antithrombotic Agents, Expert Opinion on Emerging Drugs, Jun. 1998, vol. 3, No. 1, pp. 189-208.

* cited by examiner

*Primary Examiner*—Shaojia Anna Jiang
*Assistant Examiner*—Eric S Olson
(74) *Attorney, Agent, or Firm*—Ronald G. Ort; James W. Bolcsak

(57) ABSTRACT

The present invention relates compounds of the formula A oligosaccharide-spacer-GpIIb/IIIa antagonist        (A).

The compounds of the invention have antithrombotic activity and can be used in treating or preventing thrombotic diseases.

4 Claims, 1 Drawing Sheet

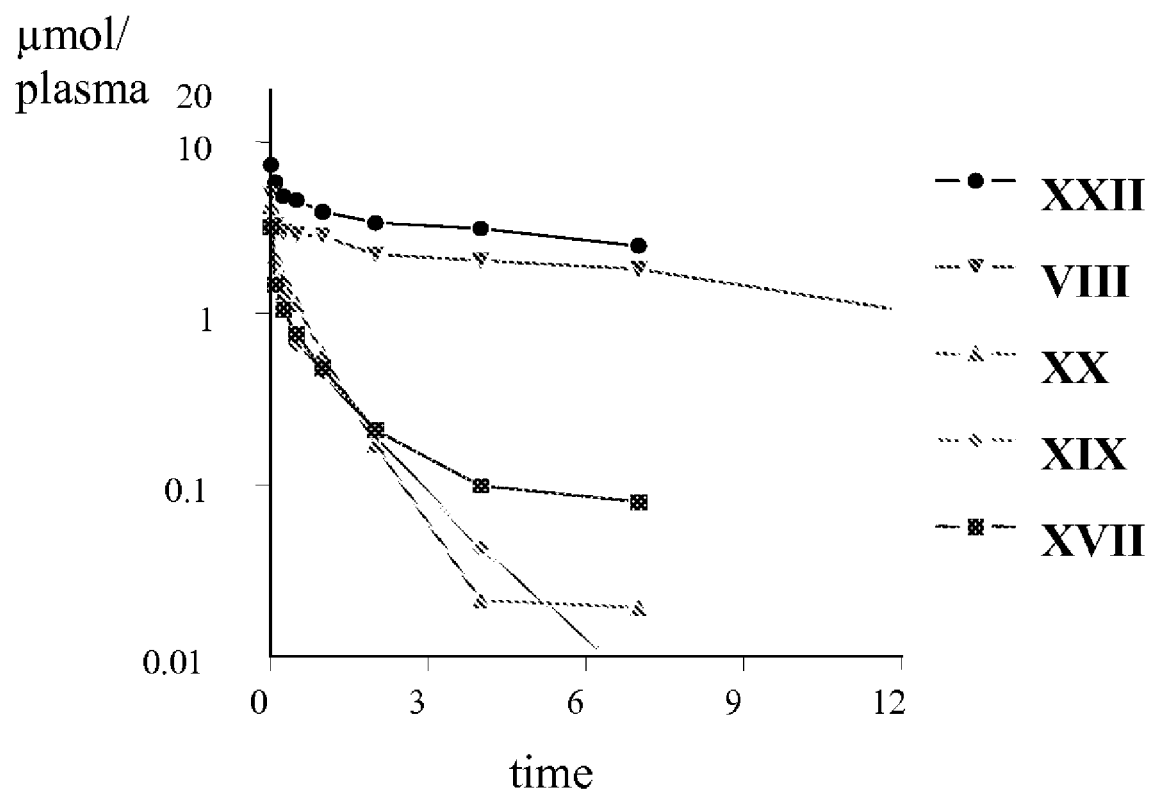
Figure 1. Kinetics of 0.5 μmol/kg in guinea pigs

US 7,576,071 B2

ANTITHROMBOTIC COMPOUND

CROSS-REFERENCE TO RELATED APPLICATIONS

This application is a continuation of International Application No. PCT/EP2005/002881, filed 3 Mar. 2005, which claims priority from European Application EP04005343.1, filed 5 Mar. 2004, the disclosures of which are incorporated herein by reference.

BACKGROUND OF THE INVENTION

The invention relates to a new antithrombotic compound, a pharmaceutical composition containing the compound as an active ingredient, as well as the use of said compound for the manufacture of medicaments.

Acute myocardial infarction, ischemia and stroke are caused by the formation of an occlusive thrombus in an atherosclerotic coronary artery. The arterial thrombus is formed by blood platelets (thrombocytes) aggregating with (increased levels of) fibrinogen. This process is associated with an excited state and imbalance of the coagulation system in which fibrinogen is cleaved into fibrin clots. Intervention in one of these primary and secondary haemostatic pathways is essential in the treatment of (arterial) thrombosis.

Serine proteases are enzymes which play an important role in the blood coagulation cascade. Members of this group of proteases are for example thrombin, trypsin, factors VIIa, IXa, Xa, XIa, XIIa, and protein C. Thrombin is the final serine protease enzyme in the coagulation cascade. The prime function of thrombin is the cleavage of fibrinogen to generate fibrin monomers, which are cross-linked to form an insoluble gel. In addition, thrombin regulates its own production by activation of factors V and VIII earlier in the cascade. It also has important actions at cellular level, where it acts on specific receptors to cause platelet aggregation, endothelial cell activation and fibroblast proliferation. Thus thrombin has a central regulatory role in haemostasis and thrombus formation. Factor Xa catalyzes the conversion of prothrombin into thrombin. Inhibition of factor Xa effectively results in inhibition of the coagulation of blood.

Platelet aggregation is triggered by several activators, not only by thrombin, but also by ADP, collagen and epinephrin. In all cases, the final common pathway leading to platelet aggregation is binding of fibrinogen to its receptor, the key membrane glycoprotein complex GPIIb/IIIa. Therefore, inhibition of fibrinogen binding to this protein is considered a very effective way of inhibiting platelet aggregation for the prevention of (arterial) thrombus formation and the treatment of thrombotic disorders.

GPIIb/IIIa ($\alpha_{IIb}\beta_3$) is a surface receptor belonging to the integrin family. Integrins are composed of two chains, an $\alpha$ subunit and a $\beta$ subunit, which are held together by noncovalent bonds in a calcium dependent manner. GPIIb constitutes the $\alpha$ subunit ($\alpha_{IIb}$) with divalent cation binding domains, whereas GPIIIa is a protypical $\beta$ subunit ($\beta_3$). Integrins have been isolated from cells throughout the body and are mediators of cell-cell and cell-substrate adhesion and signaling. There are three binding sites on GPIIb/IIIa, one that recognizes the amino sequence Arg-Gly-Asp (RGD binding site), another that recognizes Lys-Gln-Ala-Gly-Asp (KQAGD binding site) and one that recognizes Lys-Gly-Asp (KGD binding site).

On each circulating platelet, there are 35,000 to 100,000 GPIIb/IIIa complexes; most are distributed on the platelet surface, with a smaller pool in an internal reserve. The GPIIb/IIIa complex does not interact with its plasma ligands until platelets have been activated by exogenous agonists such as ADP or thrombin. When this occurs, an inside-out signal is generated that results in a conformational change in the extracellular portion of the complex that renders the molecule capable of binding fibrinogen and other ligands.

Compounds mimicking the $\alpha$-chain (RGD) and $\gamma$-chain (KQAGDV) fragments of fibrinogen may act as antagonists. Numerous potent GPIIb/IIIa antagonists based on peptidomimetic structures have been described previously.

Some (very) potent examples are Ro 435054, xemilofiban, RWJ 50042, tirofiban and lamifiban. However, a significant number of GPIIb/IIIa antagonists showing excellent potencies and pharmacological profiles in vitro, are not further developed or on hold after having reached late phase clinical trials, due to a lack of consistent control of platelet aggregation and ambiguous pharmacological behavior, (partly) caused by the short half-lives of the compounds. The short half-lives lead to large variations in plasma levels of the free drug and may contribute to interindividual variability in dose response (monitoring therapy is required).

It was further reported by H. Darius in Thromb Res. 2001, 103, S117-S124 that in all large clinical trials with GPIIb/IIIa antagonists the therapeutic effect was only minor and, moreover, even an increased mortality in the glycoprotein IIb/IIIa receptor-antagonist-treated group of patients (orally treated) had been observed. The narrow therapeutic window and limited bioavailability of the drugs, together with the still very limited knowledge about the regulation of the platelet fibrinogen receptor, were considered to be responsible for this therapeutic failure. In conclusion, there is a need for GPIIb/IIIa antagonists having a predictable antithrombotic effect, preferably with a longer half-life (to achieve consistent levels of inhibition of platelet aggregation).

BRIEF SUMMARY OF THE INVENTION

According to the present invention new compounds have now been found which are inhibitors preferably having a mixed pharmacological profile by inhibiting two key targets in both the coagulation cascade (factor Xa) and the platelet aggregation pathway (GpIIb/IIIa).

BRIEF DESCRIPTION OF THE DRAWING

FIG. 1 shows the kinetics of several compounds of this invention at 0.5 µmol/kg in guinea pigs.

DETAILED DESCRIPTION OF THE INVENTION

The compounds of this invention have the formula A oligosaccharide-spacer-GpIIb/IIIa antagonist       (A), wherein the oligosaccharide is a negatively charged oligosaccharide residue comprising four to twenty five monosaccharide units, the charge being compensated by positively charged counterions, and wherein the oligosaccharide residue is derived from an oligosaccharide which has (AT-III mediated) anti-Xa activity per se;

the spacer is a bond or an essentially pharmacologically inactive linking residue;

the GpIIb/IIIa antagonist is a residue mimicking the RGD and/or K(QA)GD fragment of fibrinogen, typically comprising an optionally esterified carboxylate moiety and a basic moiety located within the residue at a distance of 10-20 Å from each other;

or a pharmaceutically acceptable salt thereof or a prodrug or a solvate thereof.

The compounds of the invention are effective antithrombotic agents by both ATIII-mediated inhibition of coagulation factor Xa and inhibition of platelet aggregation by antagonizing the binding of fibrinogen to its receptor. When compared to the combination therapies known in the art, wherein GpIIb/IIIa inhibitors are combined with anticoagulant therapies (such as described in Expert Opin. Investig. Drugs (2003) 12(9), 1567, and in US 2003/0199457 A1), the pharmacokinetic and pharmacodynamic profiles of the compounds of the present invention lead to more consistent control of platelet aggregation and to less interindividual variability in dose response. A further advantage of the compounds of the present invention is that the pharmacological profile can be tuned: (a) by changing the type of oligosaccharide the binding to ATIII is affected, resulting in an increase or decrease of the Xa inhibitory activity, and longer or shorter half lives, respectively, (b) by changing the type of GpIIb/IIIa antagonist the inhibition of the platelet aggregation can be increased or decreased, (c) by changing the spacer length, further tuning of the individual pharmacological activities of each compound is possible.

Other conjugates comprising an oligosaccharide have been reported, being synthetic conjugates of a pentasaccharide and a direct thrombin inhibitor (Bioorg. Med. Chem. Lett. 1999, 9(14), 2013-8; WO 99/65934; WO 01/42262) or conjugates of two oligosaccharides, wherein one of the oligosaccharides displays indirect AT-III mediated anti-thrombin activity, in addition to AT-III mediated anti-Xa activity of the other oligosaccharide (EP 0,649,854). Though also antithrombotic compounds, those compounds only act on factors of the coagulation cascade. The compounds of the present invention, on the other hand, also act on the GPIIb/IIIa receptor present on the surface of circulating platelets. The mechanism of action is therefore significantly different from each of the other types of antithrombotic conjugates. With the compounds of the present invention two complementary antithrombotic therapies are available within one single drug substance.

The compounds of the present invention are useful for treating and (possibly) preventing thrombotic diseases. This includes a number of thrombotic and prothrombotic states in which the coagulation cascade is activated which include, but are not limited to, deep vein thrombosis, pulmonary embolism, thrombophlebitis, arterial occlusion from thrombosis or embolism, arterial reocclusion during or after angioplasty, restenosis following arterial injury or invasive cardiological procedures, postoperative venous thrombosis or embolism, stroke and myocardial infarction.

Any negatively charged oligosaccharide residue of four to twenty five monosaccharide units is useable in the compounds of the present invention. Suitable compounds of the invention are compounds wherein the oligosaccharide is a sulfated or phosphorylated oligosaccharide residue. Preferably, the oligosaccharide residue is derived from an oligosaccharide which has (AT-III mediated) anti-Xa activity per se, such as the oligosaccharides disclosed in EP 0,454,220, EP 0,529,715, WO 97/47659, WO 98/03554 and WO 99/36443. Preferred compounds according to the invention are compounds wherein the oligosaccharide residue has four to sixteen monosaccharide units, and most preferably is a sulfated pentasaccharide residue.

Preferred pentasaccharide residues have the structure B

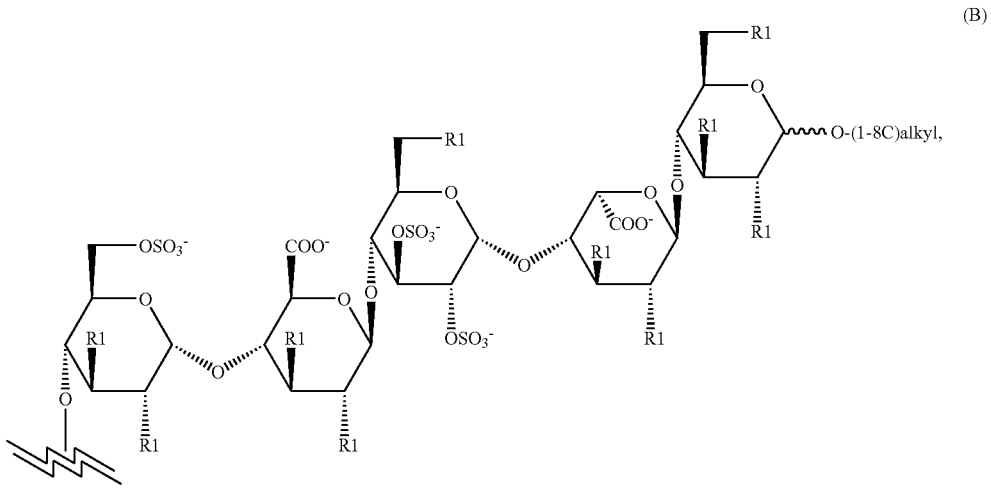

(B)

wherein R1 is independently $OSO_3^-$ or (1-8C)alkoxy and the charge being compensated by positively charged counterions.

Particularly preferred pentasaccharides have the structure C

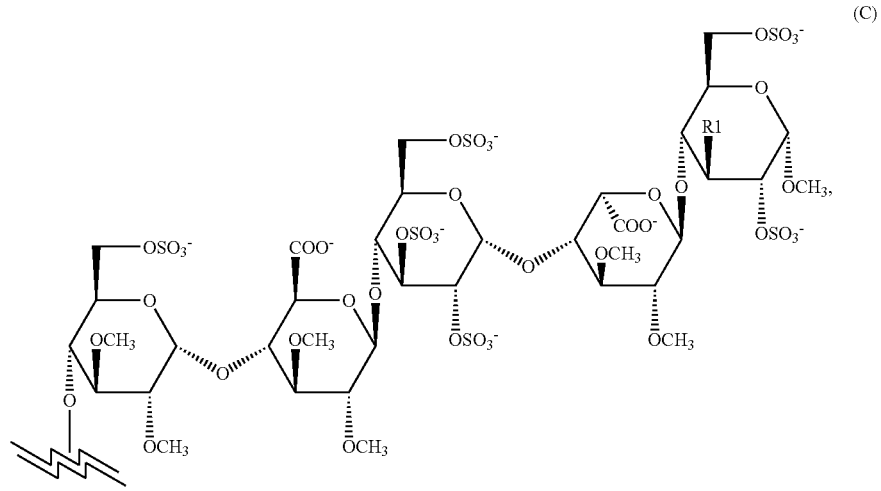

wherein R1 is $OCH_3$ or $OSO_3^-$, the charge being compensated by positively charged counterions. In the most preferred pentasaccharide of the structure C R1 is $OCH_3$.

The spacer is a bond or an essentially pharmacologically inactive linking residue. In preferred embodiments the spacer is an essentially pharmacologically inactive linking residue, preferably having 1-50 atoms, the oxygen of the oligosaccharide residue not included. The chemical nature of the spacer is of minor importance for the anti-thrombotic activity of the compounds of the invention. However, the spacer of the compounds of the invention is preferably flexible. Suitable spacers may easily be designed by a person skilled in the art. A more preferred length of the spacer is 10-35 atoms, in particular 10-28. For synthetic reasons longer spacers are considered less suitable, however, longer spacers may still successfully be applied in the compounds of the present invention. Preferred spacers contain at least one —($CH_2CH_2O$)— element. More preferred spacers contain more, preferably six —($CH_2CH_2O$)— elements. The most preferred spacer is *—($CH_2CH_2O$)$_3$—($CH_2$)$_2$—NH—C(O)—$CH_2O$—($CH_2CH_2O$)$_3$—($CH_2$)$_2$—, the end indicated with * being attached to the oxygen of the oligosaccharide residue.

The attachment site of the spacer to the GpIIb/IIIa antagonist residue may be chosen essentially arbitrarily, provided that the GpIIb/IIIa antagonist activity is not abolished. Thus, the typically present carboxylate moiety (optionally esterified) and basic moiety must remain unaffected.

In preferred compounds according to this invention, the GpIIb/IIIa antagonist residue is selected from residues derived from Ro 435054, SC 54701 (xemilofiban), RWJ 50042, sibrafiban (Ro 44 3888), lamifiban (Ro 449883), GPI 562, FK 633, tirofiban (MK 383), orbofiban (SC 57101), eptifibatide (C68 22), roxifiban (XV 459), clarofiban (RWJ 53308), SR 121787, lefradafiban (BIBU 52), lotrafiban (SB 214857), gantofiban (YM 028), T-250, EF 5077, ZD 2486, TAK 029, TP 9201, L 703014, SR 121566 (active form of SR 121787). Derivatives of said residues also include chemically modified residues, wherein the part comprising the (optionally esterified) carboxylate moiety and a basic moiety (or protected basic moiety) is retained.

Preferred GpIIb/IIIa antagonist residues have the structure D $$Y—N(H)—C(O)—X \qquad (D),$$

wherein Y is N(H)—C(O)—C(R2)(C(R2)$_2$COOH) or N(H)—C(O)—C(R2)(CH$_2$aryl)-N(H)—C(O)—C(R2)(C(R2)$_2$COOH), O-phenylene-C(R2)$_2$—C(R2)(COOH)—N(H)—C(O)—C(R2)(C(R2)$_2$COOH), O-phenylene-C(R2)$_2$—C(R2)(C(O)—R3—O—C(R2)$_2$COOH), wherein R2 is independently H or (1-4C)alkyl; and wherein aryl is phenyl, hydroxyphenyl, thiophenyl or pyridinyl and R3 is piperidinyl;

and X is benzamidine, (CH$_2$)$_2$—N(H)—C(O)-benzamidine, (CH$_2$)$_2$—C(O)—N(H)-benzamidine or

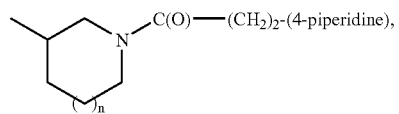

wherein n is 0, 1, 2 or 3.

The most preferred compounds of the present invention are the compounds II, V, VIII, X, XI, XII, XIII, XIV, XV and XVI as described in the examples, of which compound XIII has the highest preference.

A positively charged counterion means $H^+$, $Na^+$, $K^+$, $Ca^{2+}$, and the like. Preferably the compounds of formula (A) are in the form of their sodium salt.

The term basic moiety means any well known basic moiety, such as an amine, amidine guanidine, piperidine, and the like.

With the phrase "at a distance of 10-20 Å from each other" the spatial orientation of the two groups with respect to another is meant, not only measured along the bonds. Well known modeling techniques are available to the person skilled in the art for the determination of the distance. (See for example J. Med. Chem. 1994, 37, 2537-2551).

The term (1-8C)alkyl means a branched or unbranched alkyl group having 1-8 carbon atoms, for example methyl, ethyl, propyl, isopropyl, butyl, sec-butyl, tert-butyl, hexyl and octyl. Methyl and ethyl are preferred alkyl groups.

The term "prodrug" means a compound which is metabolized in the body into the active compound, e.g. a compound in which the basic moiety (such as an amino or benzamidino group) in the GpIIb/IIIa antagonist residue of the compound of formula A is protected, e.g. by a hydroxy, (1-6C)alkoxy or (1-6C)alkoxycarbonyl group.

Solvates according to the invention include hydrates.

The compounds of the present invention can be prepared by optionally modifying earlier described GPIIb/IIIa antagonists which are e.g. derived from Ro 435054, RWJ 50042 or SC 54701 (the pharmacologically active form of xemilofiban), tirofiban, lamifiban, or analogues thereof, with amino acids, peptidomimetics or additional functional groups (e.g. —COOH, —NH$_2$, —SH, —OH or the like) using methods generally known in the art. An example of the synthesis of such a modified RGD-analog is described in Bioorganic Chemistry 29, 357-379 (2001), where the compound is suggested as a potential vector for targeted drug delivery. According to the invention, the optionally modified GPIIb/IIIa antagonist part (a) is coupled directly to an oligosaccharide or (b) is coupled to an oligosaccharide-spacer residue or (c) is coupled to a spacer, which is subsequently is coupled to an oligosaccharide-spacer-residue (e.g. by methods known from WO 99/65934; WO 01/42262). Any suitable oligosaccharide may be used for this purpose, for example oligosaccharides known in literature (e.g. from EP 0,454,220 and EP 0,529,715, but not limited to these sources) or commercially available oligosaccharides. The oligosaccharides may be phosphorylated at an appropriate point in time by methods known in the art, e.g. as described by Buijsman, R. et al. (*Bioorg. Med. Chem. Lett.* 1999, 9, 2013-2018). The coupling of the spacer to the oligosaccharide can for instance be performed by using the methods described in EP 0,649,854.

Other examples of known GpIIb/IIIa antagonists which may serve as the (basis for the) GpIIb/IIIa antagonist part of the compounds of the present invention (but not limited to these examples): the compounds Ro 43 8857 (J. Med. Chem. 35, 4393 (1992)), Ro 48 3657, BIBL 12, FK 633, GR 144053, EMD 76 334, SR 121566, SB 208651, SC 54684, SC 52012, DMP 754, FR 158999, GR 200976, XV 788, MK 383 (tirofiban), RWJ 53308, ZD 2486, L 709780, RGD 891, T 250, C 6822, BIBU 104, SB 214857, SC 57101, G 7453, TAK 029, XV 454, XV 459, L 734 217, DMP 802, SR 121787, TP 9201, DMP 757, SC 52012, RPR 109891, YM 68128, ME 3229, ME 3230, CT 50352, MK 852, S 1197, DMP 728, SC 57345, L 738 167, GR 233548, RO 438857, TA 993, YM 337, BIBW 194, BIBU 129, BIBW 98, tetrafibricin, L 703 014, BIBU 251, GR 91669, RG 13965, G 7446, PS 028, XR 300, NSL 9403, L 756568, S 1762, L 746 223, L 767685, NSL 95301, G 4120, SB 207043, GR 83895, P246, L 739 758, XR 299, SV 873, RWJ 50228, XQ 870, EF 5154, AR 0510, G 7570, G 7442, G 7464, RWJ 52656, TAK 024, MS 180, MS 28168, XU 063, XU 065, L 734115, SM 20302, TS 943, NSL 96184, UR 12947, XU 057, L 750034, UR 3216, UR 2922, CP 4632, AR 0598, SC 79992, SC 4992, RGD 039, ME 3277, T 250, SC 57099B, SKF 106760, SKF 107260, RWJ 52654, PSA 0613, CGH 400, NSL 95317, XT 111, RWJ 27755, L 736622, SC 46749, SM 20302, YM 570029, CY 311176 and compounds described in EP 0,529,858, WO 96/20172, EP 0,496,378, EP 0,530,505, Bioorg. & Med. Chem. 3, 539 (1995), WO 93/08174, J. Am. Chem. Soc. 115, 8861 (1993), J. Med. Chem. 43, 3453 (2000), Bioorg. Med. Chem. 3, 337 (1995), U.S. Pat. Nos. 5,239,113, 5,344,957, 5,973,003, 5,703,125, WO 96/37464, WO 93/07867, U.S. Pat. No. 5,378,712, EP 445,796, U.S. Pat. Nos. 5,273,982, 5,770,575, WO 01/602813, EP 656,348, U.S. Pat. No. 5,726,185, EP 505,868, EP 560,730, U.S. Pat. No. 5,561,112, EP 513,675, U.S. Pat. No. 5,574,016, WO 94/09030, EP 478,363, U.S. Pat. Nos. 5,292,756, 5,206,373, WO 93/16994, U.S. Pat. No. 5,312,923, EP 743,302, U.S. Pat. Nos. 5,658,929, 5,880,136, 5,814,643 and 6,040,317.

Also included into the present invention are compounds comprising newly designed GpIIb/IIIa antagonist residues mimicking the RGD and/or K(QA)GD fragment of fibrinogen, typically comprising an optionally esterified carboxylate moiety and a basic moiety located within the residue at a distance of 10-20 Å from each other.

The peptide coupling, a procedural step in the above described method to prepare the compounds of the invention, can be carried out by methods commonly known in the art for the coupling—or condensation—of peptide fragments such as by the azide method, mixed anhydride method, activated ester method, the carbodiimide method, or, preferably, under the influence of ammonium/uronium salts like TBTU, especially with the addition of catalytic and racemisation suppressing compounds like N-hydroxysuccinimide and N-hydroxybenzotriazole. An overview is given in *The Peptides, Analysis, Synthesis Biology*, Vol 3, E. Gross and J. Meienhofer, eds. (Academic Press, New York, 1981).

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group, or may be introduced by demasking of an azide moiety. An overview of amino protecting groups and methods for their removal is given in the above mentioned *The Peptides, Analysis, Synthesis Biology*, Vol 3.

Amidine functions, if present, can be left unprotected in the coupling step, or can be protected using carbamate such as allyloxycarbonyl or benzyloxycarbonyl. The amidine function is preferably introduced under mild conditions by using the 1,2,4-oxadiazolin-5-one moiety as the precursor.

Carboxylic acid groups may be protected by a group commonly used in peptide chemistry for the protection of an α-carboxylic acid group, such as a tert-butyl ester. The carboxylic acid group of the modified GPIIb/IIIa antagonist is preferably protected as a benzyl ester. Removal of the protecting groups can take place in different ways, depending on the nature of those protecting groups. Usually deprotection takes place under acidic conditions and in the presence of scavengers or reductive conditions such as catalytic hydrogenation.

A prerequisite for conjugation of the GPIIb/IIIa antagonist to an oligosaccharide is the presence of an orthogonally reactive anchoring group, such as a carboxylate group, which can be coupled directly to an oligosaccharide residue or to an oligosaccharide-spacer derivative or via a spacer to an oligosaccharide-spacer derivative. To allow such conjugation in most cases additional modification of the GPIIb/IIIa antagonist is necessary.

Construction of the spacer-derived building blocks en route to compounds of the formula I can be achieved in various ways using methods known in the art, either in a linear fashion by the step-wise introduction of amino acids, their derivatives or peptidomimetics, or in convergent manner by block-coupling of intermediate constructs.

The compounds of the invention, which can occur in the form of a free base, may be isolated from the reaction mixture in the form of a pharmaceutically acceptable salt. The pharmaceutically acceptable salts may also be obtained by treating the free base of formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention may possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally. The exact dose and regimen of these compounds and compositions thereof will necessarily be dependent upon the needs of the individual subject to whom the medicament is being administered, the degree of affliction or need and the judgment of the medical practitioner. In general parenteral administration requires lower dosages than other methods of administration which are more dependent upon absorption. However, the daily dosages are for humans preferably 0.0001-10 mg per kg body weight, more preferably 0.001-1 mg per kg body weight.

The medicament manufactured with the compounds of this invention may also be used as adjuvant in (acute) anticoagulant therapy. In such a case, the medicament is administered with other compounds useful in treating such disease states, such as aspirin, clopidogrel or statins. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation, or as a spray, e.g. for use as a nasal spray.

For making dosage units, e.g. tablets, the use of conventional additives such as fillers, colorants, polymeric binders and the like is contemplated. In general any pharmaceutically acceptable additive which does not interfere with the function of the active compounds can be used.

Suitable carriers with which the compositions can be administered include lactose, starch, cellulose derivatives and the like, or mixtures thereof, used in suitable amounts.

The invention is further illustrated by the following examples.

EXAMPLES

Abbreviations Used

Aq.=aqueous
Ala=alanine
Alloc=allyloxycarbonyl
Asp=(L)-aspartate
ATIII=antithrombin III
Bn=benzyl
Boc=tert-butyloxycarbonyl
Bt=benzotriazole
t-Bu=tert-butyl
DCM=dichloromethane
DiPEA=N,N-diisopropylethylamine
DMAP=N,N-dimethylaminopyridine
DMF=N,N-dimethylformamide
EDC=1-(3-dimethylaminopropyl)-3-ethylcarbodiimide hydrochloride
Et=ethyl
ESI=electrospray ionization
HPLC=high performance liquid chromatography
HOBt=N-hydroxybenzotriazole
NMM=N-methyl morpholine
Me=methyl
MS=mass spectrometry
Phe=(L)-phenylalanyl
sat.=saturated
RT=room temperature
TBTU=2-(1H-benzotriazol-1-yl)-1,1,3,3-tetramethyluronium tetrafluoroborate
TEA=triethylamine
TFA=trifluoroacetic acid
THF=tetrahydrofuran
Tos=toluene-4-sulfonyl
TRAP=thrombin receptor agonist peptide
Tyr=L-tyrosine
Z=benzyloxycarbonyl Scheme 1

Ethyl N-(4-Cyano-benzoyl)-β-alanine (2)

A suspension of ethyl β-alanine.HCl (2.81 g, 18.3 mmol) and 4-cyano-benzoyl chloride (3.03 g, 18.0 mmol) in DCM (30 mL) was stirred overnight at RT. The mixture was diluted with EtOAc, washed with aq. citric acid (3%), sat. aq. NaHCO$_3$ and H$_2$O. Drying (MgSO$_4$) and evaporation of the solvent gave compound 2 (2.52 g, 56%).

N-(4-[1,2,4-Oxadiazol-5-onyl]-benzoyl)-β-alanine ethyl ester (3)

Compound 2 (2.50 g, 10.2 mmol) was dissolved in EtOH (70 mL). Hydroxylamine.HCl (0.99 g, 14.3 mmol) and Et$_3$N (2.49 mL, 17.3 mmol) were added and the mixture was stirred overnight at RT. The reaction was complete after refluxing for 1.5 h. The product precipitated by cooling and concentration (~10 mL) and was filtered, rinsed with EtOH and dried under vacuum.

Traces of H$_2$O were removed from the crude hydroxybenzamidine (2.8 g, 10 mmol) by coevaporation with pyridine (3×15 mL) after which it was dissolved in pyridine (100 mL). Ethyl chloroformate (1.43 mL, 15.0 mmol) was added and the mixture was stirred at reflux temperature for 18 h. The reaction was quenched by pouring into H$_2$O (200 mL), which was followed by extraction with EtOAc (3×75 mL). The organic layer was dried (MgSO$_4$) and concentrated. Residual pyridine was removed by evaporation with toluene. Recrystallization (EtOAc/hexane) afforded the product as a slightly pink-colored solid (2.48 g, 81%).

N-(4-[1,2,4-Oxadiazol-5-onyl]-benzoyl)-β-alanine (4)

Compound 3 (0.60 g, 2.0 mmol) was dissolved in a mixture of 1,4-dioxane/H$_2$O (10 mL, 1/1, v/v). Aq. NaOH (2.0 mL, 2N) was added and the mixture was stirred for 3 h at RT. The reaction mixture was neutralized with Dowex H$^+$ and filtered. The filtrate was concentrated under reduced pressure and the resulting white solid was dried under vacuum. Yield 0.51 g (93%).

1-Azido-1-deoxy-tetraethylene glycol (5)

Tetraethylene glycol (90 g, 0.46 mol) was cooled to 0° C. and a solution of sodium hydroxide (3.0 g, 75 mmol) in 10 mL of H$_2$O was added, followed by the addition of 100 mL of THF. The mixture was vigorously stirred for 30 min. p-Toluenesulfonylchloride (8.8 g, 46 mmol) in 50 mL of THF was slowly added at 0° C. under vigorous stirring to keep a homogeneous mixture. After stirring for 5 h, the mixture was poured into 400 mL of H$_2$O. The solution was extracted with DCM (4×20 mL). The combined organic layers were washed with H$_2$O (20 mL) and brine (20 mL) and dried (MgSO$_4$). After filtration the solvents were removed under reduced pressure to afford the monotosylate as an oil.

The crude compound was dissolved in a mixture of EtOH (120 mL) and H$_2$O (18 mL). Sodium azide (3.25 g, 50 mmol) was added and the mixture was stirred at 60° C. overnight. The EtOH was evaporated in vacuo (50 mbar, 50° C.) and 150 mL of EtOAc was added. The solution was washed with brine (20 mL) and dried over MgSO$_4$. After filtration the solvent was removed under reduced pressure (50 mbar, 50° C.), to give the azide 5 as an oil (6.25 g, 62% yield over the two steps).

tert-Butyl 15-aza-3,6,9,12-tetraoxa-pentadecanoate (6)

Compound 5 (1.15 g, 5.25 mmol) was dissolved in toluene (10 mL). To the solution was added a 50% aq. solution of sodium hydroxide (12.5N, 5 mL), tetrabutylammonium hydrogensulfate (0.34 g, 1.05 mmol) and tert-butyl bromoacetate (4.27 mL, 26.3 mmol). The suspension was vigorously stirred at RT. After 3 h the mixture was diluted with EtOAc (10 mL), washed with brine (10 mL), hydrochloric acid (2N, 5 mL) and H$_2$O (5 mL). The aq. layers were extracted with EtOAc after which the combined organic layers were dried (MgSO$_4$). After concentration, the crude product was purified by silica gel (20 g) column chromatography (eluent: heptane→EtOAc, 1/0-→0/1). Concentration of the appropriate fractions afforded the azide as a pale yellow oil (1.25 g, 71%). Rf 0.8 (EtOAc/MeOH, 95/5, v/v).

Reduction of the azide was effected by hydrogenation over 10% Pd/C (100 mg) in EtOH (30 mL) containing acetic acid (0.2 mL). After 4 h the catalyst was removed by filtration over two layers of Whatman GF/A filter. The filtrate was concentrated, dissolved in DCM (25 mL) and treated with Argonaut MP carbonate resin to remove the acetic acid. The resin was removed by filtration and evaporation of the solvent gave compound 6 in a yield of 1.17 g (100%).

tert-Butyl(N-benzyloxycarbonyl-L-phenylalanyl)-15-aza-3,6,9,12-tetraoxa-pentadecanoate (7)

Compound 6 (3.60 g, 11.7 mmol) and Z-Phe-OH (3.51 g, 11.7 mmol) were dissolved in DCM (30 mL). HOBt (1.39 g, 11.7 mmol), EDC (2.83 g, 14.0 mmol) and TEA (3.38 mL, 23.4 mmol) were subsequently added and the solution was allowed to stir overnight. The reaction mixture was diluted with EtOAc (30 mL) and rinsed with sat. aq. NaHCO$_3$ (2×10 mL), 5% aq. citric acid (10 mL) and H$_2$O (10 mL). The organic phase was dried (MgSO$_4$) and concentrated under reduced pressure. Purification was effected by silica gel (75 g) column chromatography (eluent: EtOAc-→EtOAc/MeOH, 95/5, v/v), to give compound 7 as a colorless oil (4.95 g, 72%). Rf 0.5 (EtOAc/MeOH, 95/5, v/v).

tert-Butyl(L-phenylalanyl)-15-aza-3,6,9,12-tetraoxa-pentadecanoate (8)

Compound 7 (2.42 g, 4.11 mmol) was dissolved in EtOH (100 mL) containing acetic acid (0.4 mL) and stirred under an atmosphere of H$_2$ in the presence of 10% Pd/C (0.1 g). After 16 h, the mixture was filtered and concentrated. Acetic acid was removed by repeated concentration of the product in toluene and treatment with Argonaut MP carbonate resin (1.3 g) in DCM (20 mL). Filtration of the resin and evaporation of the solvent afforded compound 8 as a colorless oil (1.69 g, 90%). Rf 0.05 (EtOAc/MeOH, 95/5, v/v).

tert-Butyl(N-tert-butyloxycarbonyl-O-benzyl-L-aspartyl-L-phenylalanyl)-15-aza-3,6,9,12-tetraoxa-pentadecanoate (9)

Compound 8 (1.69 g, 3.71 mmol) was coupled to Boc-Asp$^{Bn}$-OH (1.20 g, 3.71 mmol) as described earlier for the synthesis of compound 7, using NMM (0.84 mL, 7.4 mmol at pH 8.3) instead of TEA. After work-up, a yellow oil was obtained which was purified by silica gel (50 g) column chromatography (eluent: EtOAc/heptane, 2/1→EtOAc/MeOH, 95/5, v/v), to give compound 9 as a colorless oil (2.30 g, 82%). Rf 0.6 (DCM/MeOH, 9/1, v/v).

tert-Butyl(O-benzyl-L-aspartyl-L-phenylalanyl)-15-aza-3,6,9,12-tetraoxa-pentadecanoate (10)

Boc-protected compound 9 (1.09 g, 1.43 mmol) was treated with a 1.5 N solution of hydrochloric acid in EtOAc (10 mL). After stirring for 100 min. at RT the reaction mixture was cooled (0° C.) and neutralized by pouring into a cooled solution of sat. aq. NaHCO$_3$ (15 mL). The aq. layer was extracted with EtOAc (2×10 mL), the combined organic layers were washed with H$_2$O (10 mL) and dried (MgSO$_4$). Concentration afforded crude compound 10 which was used without purification in the next reaction. Rf 0.2 (EtOAc/MeOH, 95/5, v/v).

tert-Butyl({N-(4-[1,2,4-oxadiazol-5-onyl]-benzoyl)-β-alanyl}-O-benzyl-L-aspartyl-L-phenylalanyl)-15-aza-3,6,9,12-tetraoxa-pentadecanoate (11)

Carboxylic acid 4 (0.12 g, 0.42 mmol) and amine 10 (crude, max. 0.40 mmol) were dissolved in DMF (5 mL). HOBt (50 mg, 0.42 mmol), EDC (94 mg, 0.50 mmol) and NMM (88 μL, 0.61 mmol) were subsequently added and the solution was allowed to stir overnight. The brown solution was diluted with a mixture of EtOAc and 2-butanol (10 mL, 1/1, v/v) and extracted with 3% citric acid (5 mL), sat. NaHCO$_3$ (5 mL) and brine (5 mL). The aq. phases were consecutively extracted with EtOAc and the combined organic layers dried over MgSO$_4$. Removal of the solvent gave crude compound 11 (0.27 g, 78%), which was used without purification in the next reaction. Rf 0.2 (DCM/MeOH, 9/1, v/v).

({N-(4-[1,2,4-Oxadiazol-5-onyl]-benzoyl)-β-alanyl}-O-benzyl-L-aspartyl-L-phenylalanyl)-15-aza-3,6,9,12-tetraoxa-pentadecanoic acid (12)

Compound 11 (0.2 g, crude, max. 0.22 mmol) was stirred in a mixture of DCM (5 mL) and TFA (3 mL). After 2 h the solution was concentrated and remains of TFA were removed by repeated concentration in toluene (3×5 mL). The product was purified by preparative HPLC-MS to give compound 12 in pure form (0.11 g, 56% over the three steps from 9).

tert-Butyl({N-(4-amidinobenzoyl)-β-alanyl}-L-aspartyl-L-phenylalanyl)-15-aza-3,6,9,12-tetraoxa-pentadecanoate (I)

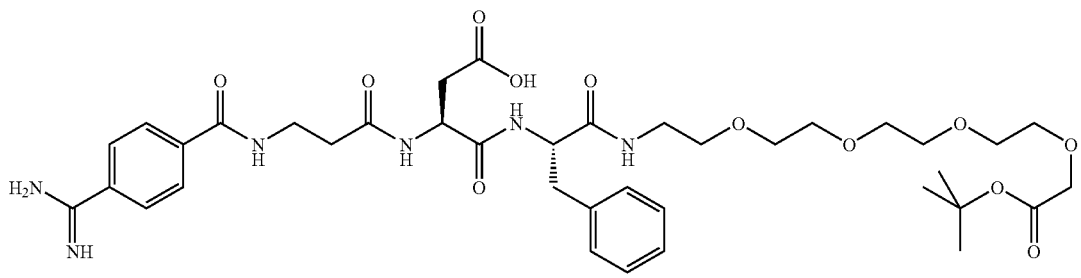

(I)

Compound 11 (65 mg, crude, max. 71 μmol) was dissolved in a mixture of EtOH (10 mL), H$_2$O (2 mL) and acetic acid (0.1 mL). 10% Pd/C (50 mg) was added and the mixture was stirred overnight under an atmosphere of H$_2$ gas. The catalyst was removed by filtration over two layers of Whatman GF/A filter and the filtrate was concentrated. The product was obtained in pure form by applying preparative HPLC-MS and lyophilization. Yield 7.7 mg (14%. ESI-MS: 787 [M+H]$^+$.

General Procedure for Conjugation of Spacer-Derived GPIIb/IIIa Antagonists 12, 23, 31, 33, 43, 50, 52, 54, 62 to Pentasaccharide 63, see Scheme 8 and 9

The spacer-derived carboxylic acid (33 μmol) (i.e. compound 12, 23, 31, 33, 43, 50, 52, 54 or 62) was dried by coevaporation with DMF (2×2 mL), dissolved in DMF (1 mL) and stirred in the presence of TBTU (10.5 mg, 33 μmol) and DiPEA (5.7 μL, 33 μmol), under an atmosphere of N$_2$. After 1 h, the aminospacer-containing pentasaccharide 63 (56 mg, 31 μmol) was added. The reaction mixture was stirred overnight at RT and analyzed by ion exchange (Mono-Q) and reversed phase (Luna C18) chromatography. After complete consumption of the pentasaccharide, the reaction mixture was concentrated (<50° C., 15 mmHg).

The (crude) product (10 mg/mL in H$_2$O) was deprotected by hydrogenation (H$_2$) over 10% Pd/C (an equal amount in weight was added with respect to the crude product). After 16 h the solution was degassed, filtered over a 0.45 μM HPLC filter and concentrated under reduced pressure (<50° C., 15 mmHg). The conjugate was purified by ion exchange chromatography (Q-sepharose, buffer: H$_2$O→2M NaCl), followed by desalting with a Sephadex G25-column (H$_2$O) and lyophilization.

Methyl O-2,3-di-O-methyl-4-O-{({N-(4-amidi-nobenzoyl)-β-alanyl}-L-aspartyl-L-phenylalanyl)-(15-aza-3,6,9,12-tetraoxa-pentadecanoyl)-(1-aza-4,7,10-trioxadodecyl)}-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (II)

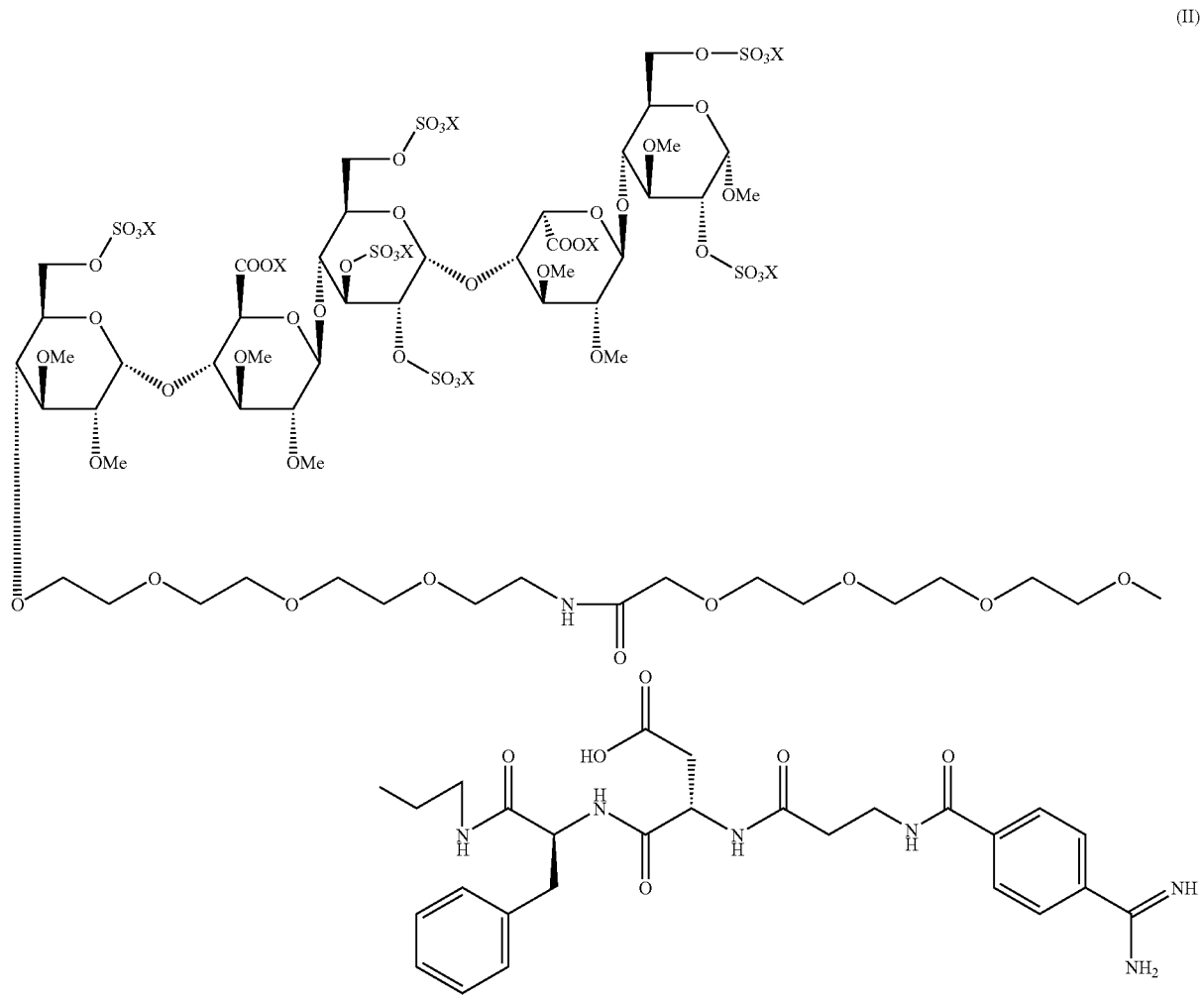

(II)

X = Na$^+$

The product was obtained by conjugation of 12 (21.4 mg, 24.8 μmol) with pentasaccharide 63 (42.4 mg, 23.6 μmol), purification and deprotection according to the general procedure. White solid, yield 34 mg (42%, 2 steps). $^1$H-NMR (D$_2$O, 600 MHz, HH-COSY): δ 3.38-3.32 (8×s, 34H, 8×OMe); ring D: 5.36 (d, 1H, H1), 4.18 (m, 1H, H6a), 4.04 (d, 1H, H6b), 3.80 (m, 1H, H5), 3.47 (m, 1H, H3), 3.27 (dd, 1H, H2); ring E: 4.59 (d, 1H, H1), 3.82 (m, 1H, H4), 3.62 (m, 1H, H5), 3.45 (m, 1H, H3), 3.15 (m, 1H, H2); ring F: 5.27 (d, 1H, H1), 4.49 (t, 1H, H3), 4.33 (d, 1H, H6a), 4.20 (m, 1H, H2), 4.08 (m, 1H, H6b), 3.86 (t, 1H, H4); ring G: 4.92 (bs, 1H, H1), 4.54 (d, 1H, H5), 4.07 (m, 1H, H4), 3.74 (1H, dd, H3), 3.37 (m, 1H, H1); ring H: 4.99 (d, 1H, H1), 4.25 (m, 1H, H2), 4.22 (m, 1H, H6a), 4.17 (dd, 1H, H6b), 3.92 (ddd, 1H, H5), 3.66 (t, 1H, H4), 3.58 (m, 1H, H3); spacer: 3.96 (s, 2H, C(O)CH$_2$O), 3.62-3.51 (m, 26H, 13×CH$_2$O), 3.33-3.30 (m, 4H, OCH$_2$CH$_2$NHCH(O)CH$_2$, OCH$_2$CH$_2$NHC(O)-Phe), 3.25 (m, 1H, OCH$_{2a}$CH$_2$NHC(O)-Phe), 3.17 (m, 1H, OCH$_{2b}$CH$_2$NHC(O)-Phe); peptide: 7.84 (d, 2H, H$_{arom}$ benzamidine), 7.79 (d, 2H, H$_{arom}$ benzamidine), 7.25 (t, 2H, H$_{arom}$ Phe), 7.20 (t, 1H, H$_{arom}$ Phe), 7.09 (d, 2H, H$_{arom}$ Phe), 4.51 (dd, 1H, CH Asp), 4.38 (t, 1H, CH Phe), 3.60 (m, 2H, CH$_2$N β-Ala), 2.83 (dAB, 2H, CH$_2$ Phe), 2.52 (t, 2H, C(O)CH$_2$ β-Ala), 2.44 (dAB, 2H, CH$_2$ Asp).

ESI-MS: Calculated: 2511.4; found: m/z 1267.9 [M+H+Na]$^{2+}$, 1256.9 [M+2H]$^{2+}$, 1245.9 [M+2H—Na]$^{2+}$, 852.9 [M+H+2Na]$^{3+}$, 845.5 [M+2H+Na]$^{3+}$, 838.3 [M+3H]$^{3+}$, 639.9 [M+2H+2Na]$^{4+}$, 1232.8 [M–2Na]$^{2-}$, 1221.7 [M–3Na+H]$^{2-}$, 1210.8 [M–4Na+2H]$^{2-}$, 1199.8 [M–5Na+3H]$^{2-}$, 814.1 [M–3Na]$^{3-}$.
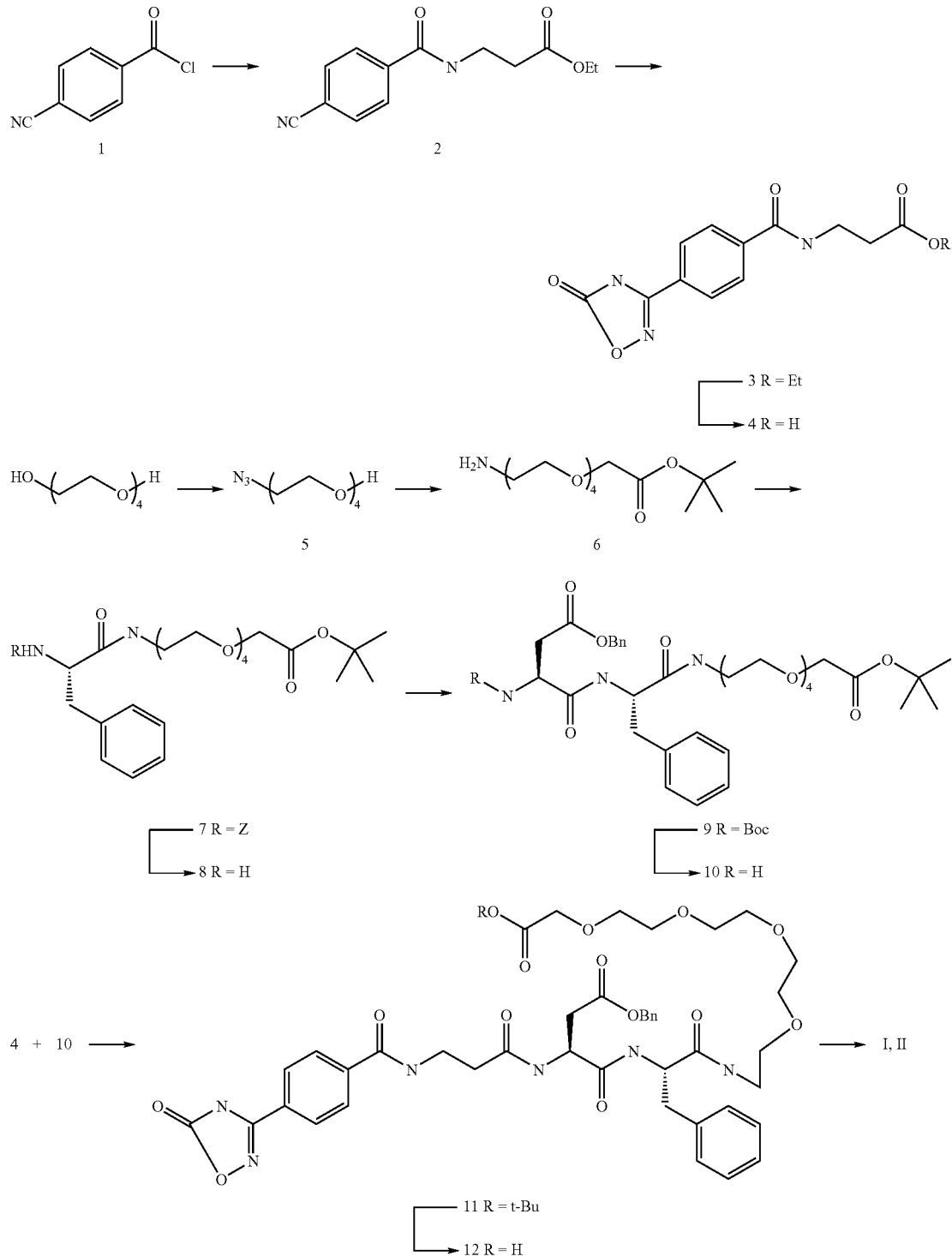

Scheme 2

4-(tert-Butyloxycarbonylamino)-benzonitrile (14)

4-Aminobenzonitrile (13, 2.95 g, 25 mmol) and di-tert-butyl dicarbonate (8.0 mL, 35 mmol) were stirred in a mixture of THF (50 mL) and pyridine (4 mL) at 75° C. After 16 h the red colored reaction mixture was cooled, diluted with EtOAc (30 mL) and washed with hydrochloric acid (1N, 15 mL), sat. aq. NaHCO$_3$ (15 mL) and brine (15 mL). The organic layer was dried (MgSO$_4$) and concentrated. The dark brown oil was purified by silica gel (75 g) column chromatography (eluent: EtOAc/heptane, 1/5-→1/2, v/v) which afforded compound 14 as an orange oil (3.25 g, 60%), containing ~30% bis-Boc protected product. The latter mixture was used without further purification in the next reaction.

4-(1,2,4-Oxadiazol-5-onyl)-aniline (16)

Compound 14 (3.25 g, 14.9 mmol) was converted into oxadiazolone 15 as described earlier for the preparation of compound 3. The resulting crude light orange solid was stirred for 5 h in a mixture of DCM (15 mL) and TFA (8 mL). Concentration under reduced pressure and evaporation with toluene (2×10 mL) gave a brown solid which was purified by silica gel (40 g) column chromatography (eluent: EtOAc) to yield compound 16 (1.81 g, 69% over the three steps). Rf 0.5 (EtOAc).

N-[4-(1,2,4-Oxadiazol-5-onyl)-phenyl]-succinamic acid (17)

Aniline derivative 16 (0.89 g, 5.0 mmol) was dissolved in pyridine (25 mL). Succinic anhydride (0.75 g, 7.5 mmol) was added together with 4-N,N,-dimethylaminopyridine (63 mg, 0.5 mmol) and the mixture was stirred overnight at 100° C. The solution was concentrated under reduced pressure and the pale brown solid was recrystallized from a mixture of EtOH/MeOH/H$_2$O (60 mL, 5/35/1, v/v/v). After filtration, the mother liquid was concentrated to ~10 mL to give carboxylic acid 17 as a solid which was dried under vacuum at 50° C. for 16 h. Yield 1.28 g (92%). Rf 0.3 (DCM/MeOH/AcOH, 100/10/1, v/v/v).

tert-Butyl(N-tert-butyloxycarbonyl-O-benzyl-L-aspartyl)-15-aza-3,6,9,12-tetraoxa-pentadecanoate (18)

Compound 6 (0.94 g, 3.1 mmol) and Boc-Asp$^{Bn}$-OH (0.99 g, 3.1 mmol) were dissolved in DCM (8 mL). HOBt (0.36 g, 3.1 mmol), EDC (0.74 g, 3.8 mmol) and NMM (0.34 mL, 6.2 mmol) were subsequently added and the solution was allowed to stir overnight. The reaction mixture was diluted with EtOAc (10 mL) and rinsed with sat. aq. NaHCO$_3$ (2×5 mL), 5% aq. citric acid (5 mL) and H$_2$O (5 mL). The organic phase was dried (MgSO$_4$) and concentrated under reduced pressure. Purification was established by silica gel (20 g) column chromatography (eluent: EtOAc/heptane, 3/1-→1/0, v/v), to give compound 18 as a colorless oil (1.15 g, 61%). Rf 0.7 (EtOAc/MeOH, 95/5, v/v).

tert-Butyl(O-benzyl-L-aspartyl)-15-aza-3,6,9,12-tetraoxa-pentadecanoate (19)

Compound 18 (0.51 g, 0.83 mmol) was treated during 45 min. according to the same reaction conditions and work-up procedure as described earlier for the synthesis of compound 10. Product 19 was used in the next reaction without further purification.

tert-Butyl N-{[4-(1,2,4-oxadiazol-5-onyl)-phenyl]-succinamyl-(O-benzyl-L-aspartyl)}-15-aza-3,6,9,12-tetraoxa-pentadecanoate (20)

Compound 17 (0.30 mmol) and 19 (0.30 mmol) were coupled as described earlier for the synthesis of 11. Crude compound 20 (0.17 g, 75%) was used without further purification in the next reaction. Rf 0.3 (DCM/MeOH, 9/1, v/v).

tert-Butyl N-{(4-benzamidino)-succinamyl}-L-aspartyl-15-aza-3,6,9,12-tetraoxa-pentadecanoate (III)

Catalytic hydrogenation of 20 (32 mg, 41 µmol) was effected in a mixture of EtOH/H$_2$O/AcOH. Filtration, con

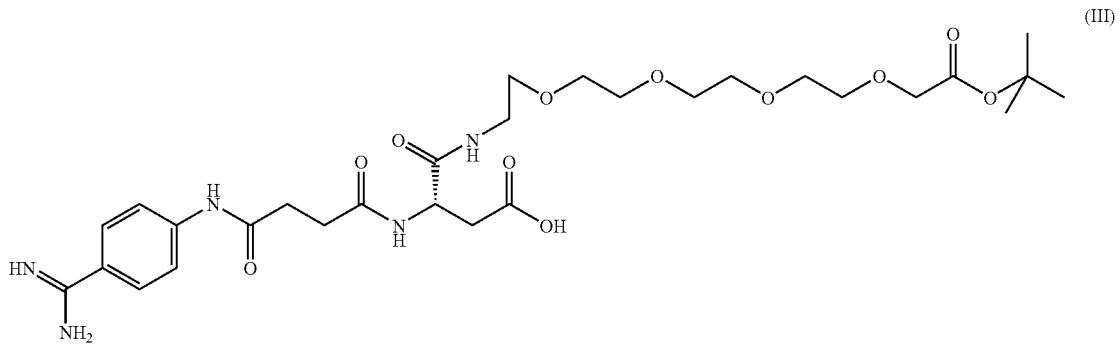

centration and purification by preparative HPLC-MS gave spacer derivative III as a white solid. Yield 20 mg (77%). ESI-MS: 640 [M+H]$^+$.

tert-Butyl N-[4-(1,2,4-oxadiazol-5-onyl)-phenyl]-succinamyl-(O-benzyl-L-aspartyl-L-phenylalanyl)-15-aza-3,6,9,12-tetraoxa-pentadecanoate (22)

Oxadiazolone 17 (24 mg, 88 µmol) and crude amine 10 (max. 58 mg, 88 µmol) were coupled as described earlier for the synthesis of compound 11. Crude product 22 was used in the next reaction without further purification. Rf 0.6 (DCM/MeOH, 9/1, v/v).

N-[4-(1,2,4-Oxadiazol-5-onyl)-phenyl]-succinamyl-(O-benzyl-L-aspartyl-L-phenylalanyl)-15-aza-3,6,9,12-tetraoxa-pentadecanoic acid (23)

Crude compound 22 (max. 88 μmol) was stirred in a mixture of DCM (1.0 mL) and TFA (1.0 mL). After 2 h the solution was concentrated and the product was purified by preparative HPLC. Concentration of the appropriate fractions afforded compound 23 in a yield of 31 mg (41% over the last three steps).

tert-Butyl N-{(4-benzamidino)-succinamyl}-L-aspartyl-L-phenylalanyl-15-aza-3,6,9,12-tetraoxa-pentadecanoate (IV)

(IV)

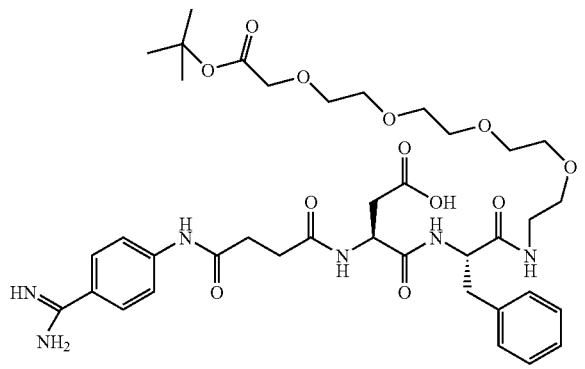

Crude compound 22 (max. 80 mg, 87 μmol) was deprotected by catalytic hydrogenation over 10% Pd/C (50 mg) in a mixture of EtOH (7 mL) and H$_2$O (1 mL). After 24 h, the mixture was filtered and concentrated and the crude product was purified by preparative HPLC. Compound IV was isolated as a white foam after lyophilization in a yield of 10.5 mg (15%). ESI-MS: 787 [M+H]$^+$.

Methyl O-2,3-di-O-methyl-4-O-{[N-(4-benzamidyl)-succinamyl]-L-aspartyl-L-phenylalanyl)-(15-aza-3,6,9,12-tetraoxa-pentadecanoyl)-(1-amino-4,7,10-trioxadodecyl)}-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (V)

(V)

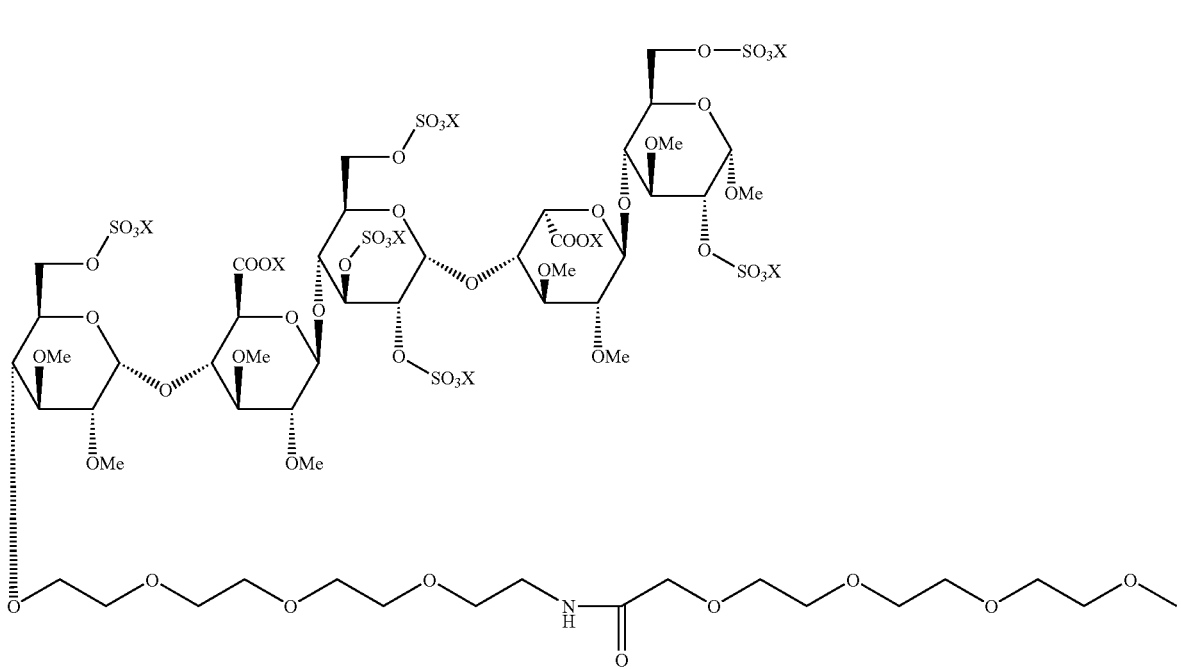

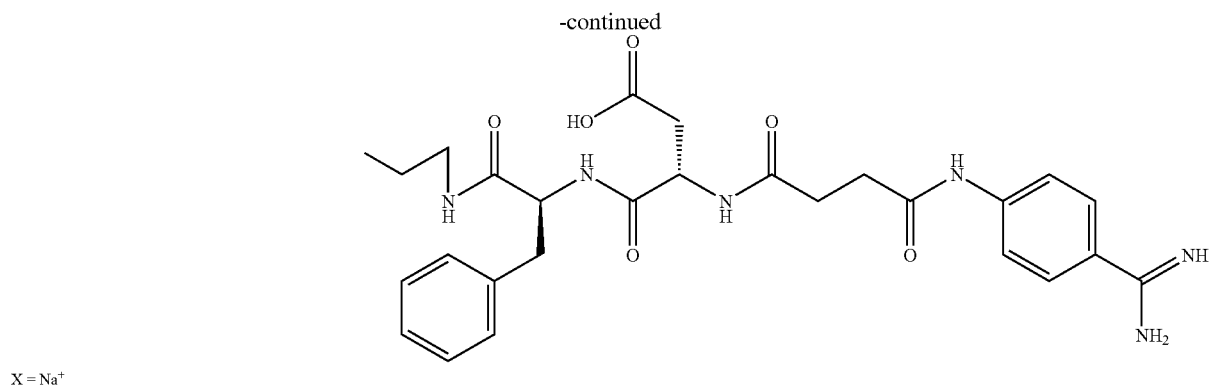

X = Na+

Conjugation of carboxylic acid 23 (30.0 mg, 34.8 μmol) to pentasaccharide 63 (59.4 mg, 56.4 μmol), followed by purification and deprotection was effected according to the general procedure. Conjugate V was obtained as a white solid, yield 37.5 mg (48%, 2 steps). $^1$H-NMR (D$_2$O, 600 MHz, HH-COSY): δ 3.43-3.32 (8×s, 34H, 8×OMe); ring D: 5.36 (d, 1H, H1), 4.21 (m, 1H, H6a), 4.05 (d, 1H, H6b), 3.79 (m, 1H, H5), 3.48 (m, 1H, H3), 3.33 (m, 1H, H4), 3.20 (dd, 1H, H2); ring E: 4.58 (d, 1H, H1), 3.79 (m, 1H, H4), 3.65 (m, 1H, H5), 3.48 (m, 1H, H3), 3.15 (m, 1H, H2); ring F: 5.26 (d, 1H, H1), 4.48 (t, 1H, H3), 4.32 (d, 1H, H6a), 4.22 (m, 1H, H6b), 4.15 (dd, 1H, H2), 4.08 (m, 1H, H5), 3.84 (t, 1H, H4); ring G: 4.98 (bs, 1H, H1), 4.55 (d, 1H, H5), 4.07 (m, 1H, H4), 3.73 (1H, dd, H3), 3.37 (m, 1H, H2); ring H: 4.98 (d, 1H, H1), 4.25 (dd, 1H, H2), 4.21 (m, 1H, H6a), 4.17 (m, 1H, H6b), 3.92 (ddd, 1H, H5), 3.66 (t, 1H, H4), 3.58 (m, 1H, H3); spacer: 3.96 (s, 2H, C(O)CH$_2$O), 3.61-3.51 (m, 26H, 13×CH$_2$O), 3.38-3.30 (m, 4H, OCH$_2$CH$_2$NHCH(O)CH$_2$, OCH$_2$CH$_2$NHC(O)-Phe), 3.19 (m, 1H, OCH$_{2a}$CH$_2$NHC(O)-Phe), 3.12 (m, 1H, OCH$_{2b}$CH$_2$NHC(O)-Phe); peptide: 7.69 (d, 2H, H$_{arom}$ benzamidine), 7.63 (d, 2H, H$_{arom}$ benzamidine), 7.25 (t, 2H, H$_{arom}$ Phe), 7.20 (t, 1H, H$_{arom}$ Phe), 7.09 (d, 2H, H$_{arom}$ Phe), 4.44 (dd, 1H, CH Asp), 4.38 (t, 1H, CH Phe), 2.90 (dAB, 2H, CH$_2$ Phe), 2.75 (m, 2H, CH$_2$ succinyl), 2.55 (m, 2H, CH$_2$ succinyl), 2.43 (dAB, 2H, CH$_2$ Asp).

ESI-MS: Calculated: 2511.4; found: m/z 1267.8 [M+H+Na]$^{2+}$, 1256.8 [M+2H]$^{2+}$, 1245.8 [M+2H–Na]$^{2+}$, 852.8 [M+H+2Na]$^{3+}$, 845.5 [M+2H+Na]$^{3+}$, 838.2 [M+3H]$^{3+}$, 6.39.9 [M+2H+2Na]$^{4+}$, 1232.7 [M–2Na]$^{2-}$, 1221.7 [M–3Na+H]$^{2-}$, 1210.7 [M–4Na+2H]$^{2-}$, 1199.7 [M–5Na+3H]$^{2-}$, 814.1 [M–3Na]$^{3-}$.

Scheme 2. Synthesis of III and IV

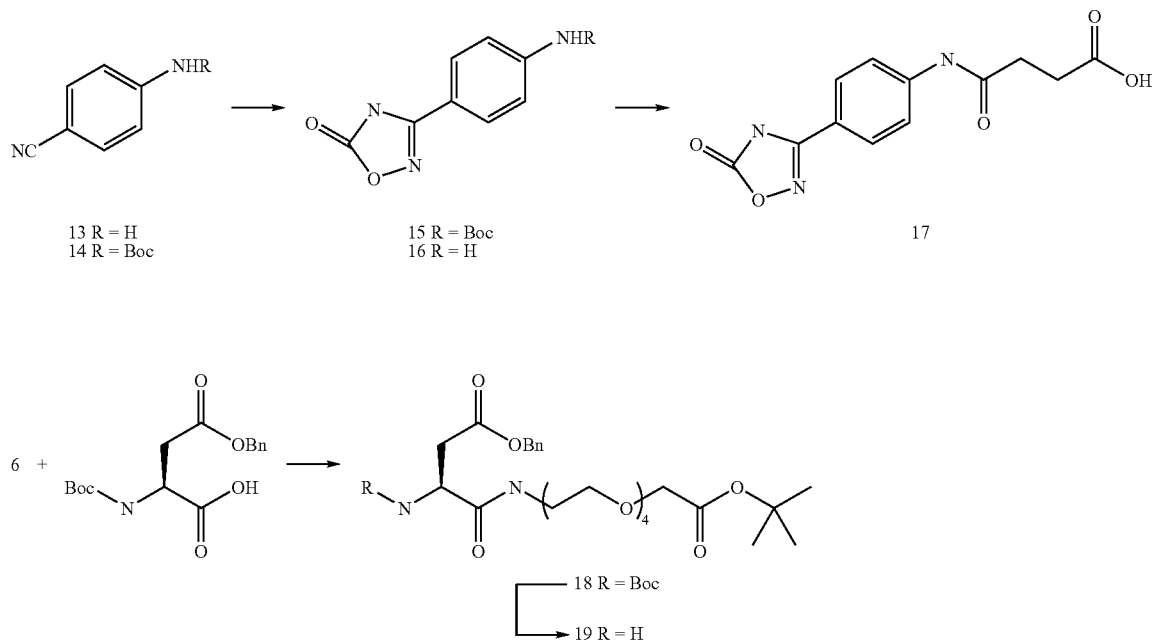

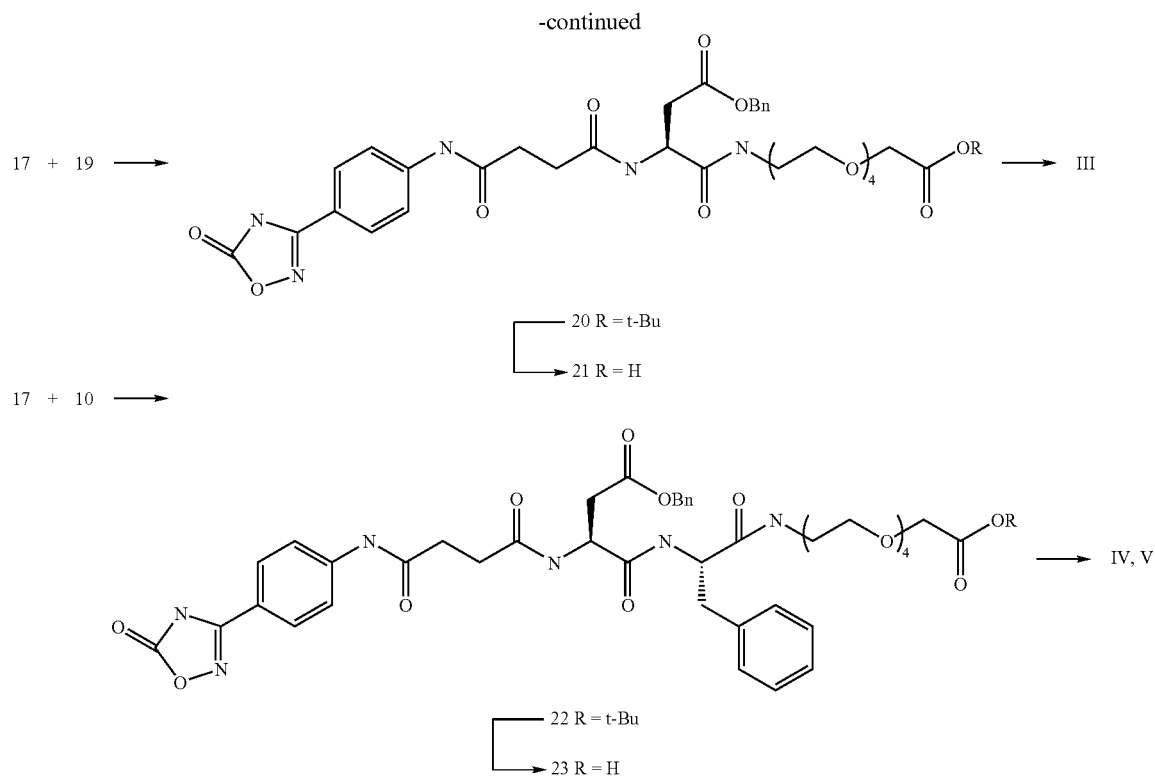

- 20 R = t-Bu
- 21 R = H

- 22 R = t-Bu
- 23 R = H

Scheme 3

Ethyl N-3-[4-(N-tert-butyloxycarbonyl)-piperidinepropionyl]-(R)-(−)-nipecotate (26)

A mixture of 3-(N-Boc-piperidyl)-propionic acid (24, 1.00 g, 3.89 mmol), TBTU (1.38 g, 4.28 mmol) and DiPEA (2.70 mL, 15.6 mmol) in DCM (20 mL) was stirred for 5 min. Next, ethyl (R)-nipecotate (L)-tartrate salt (25, 0.61 g, 3.89 mmol) was added and the solution was stirred for 2 h. The reaction was quenched with 5% aq. NaHCO$_3$ (20 mL), washed with 3% aqueous citric acid (20 mL) and H$_2$O (20 mL). The aq. phases were extracted with DCM (3×10 mL) and the combined organic layers were dried (MgSO$_4$). Compound 26 (2.34 g) was obtained as a brown-yellowish oil, which was used without further purification in the next reaction. Rf 0.7 (EtOAc/MeOH, 93/7, v/v).

Ethyl N-3-[4-(N-benzyloxycarbonyl)-piperidinepropionyl]-(R)-(−)-nipecotate (28)

Crude compound 26 (max. 3.89 mmol) was stirred in a mixture of DCM (10 mL) and TFA (10 mL). After 1 h the solution was concentrated under reduced pressure. Traces of TFA were removed by repeated concentration in toluene (3×10 mL). Subsequently, crude piperidine derivative 27 was dissolved in DCM (10 mL), followed by the addition of DiPEA (2.02 mL, 11.7 mmol) and (N)-benzyloxycarbonyloxy-succinidmide (1.94 g, 7.79 mmol). After stirring overnight the reaction mixture was diluted with EtOAc (20 mL), rinsed with sat. aq. NaHCO$_3$ (10 mL), 3% aq. citric acid and H$_2$O (10 mL). The organic phase was dried over MgSO$_4$ and concentrated furnishing Z-protected compound 28 as a colorless oil. (1.37 g, 82% over the three steps). Rf 0.5 (EtOAc).

N-3-[4-(N-benzyloxycarbonyl)-piperidinepropionyl]-(R)-(−)-nipecotic acid (29)

A solution of compound 28 (0.35 g, 3.14 mmol) in 1,4-dioxane (20 mL) and 0.5M NaOH (20 mL) was stirred for 1 h. Neutralization by Dowex 50 WX4-H$^+$ ion-exchange, filtration and concentration afforded carboxylic acid derivative 29 as a slightly yellowish colored oil (1.27 g, 100%). Rf 0.05 (EtOAc).

tert-Butyl{N-3-[4-(N-benzyloxycarbonyl)-piperidinepropionyl]-(R)-(−)-nipecotyl}-(O-benzyl-L-aspartyl)-15-aza-3,6,9,12-tetraoxa-pentadecanoate (30)

A mixture of compound 29 (0.24 g, 0.60 mmol) and crude 19 (max. 0.60 mmol), together with EDC (0.14 g, 0.72 mmol) and NMM (90 µL, 0.78 mmol) in DCM (5 mL) was stirred for 5 h. The solution was diluted with DCM (10 mL) and washed with sat. aq. NaHCO$_3$ (10 mL), 3% aq. citric acid and H$_2$O (10 mL). The organic phase was dried over MgSO$_4$ and concentrated. Crude 30 was purified by silica gel (5 g) column chromatography (eluent: EtOAc/heptane/MeOH, 2/1/0-→9/0/1, v/v/v). Yield 0.29 g (53%). Rf 0.6 (EtOAc/MeOH, 7/1, v/v).

{N-3-[4-(N-benzyloxycarbonyl)-piperidinepropionyl]-(R)-(−)-nipecotyl}-(O-benzyl-L-aspartyl)-15-aza-3,6,9,12-tetraoxa-pentadecanoic acid (31)

Compound 30 (0.29 g, 0.32 mmol) was stirred in a mixture of DCM (5 mL) and TFA (5 mL). After 3 h the mixture was concentrated and repeatedly evaporated on toluene (3×10 mL). The product was purified by preparative HPLC, to give 31 in a yield of 0.23 g (86%).

tert-Butyl{N-3-[4-(N-benzyloxycarbonyl)-piperidinepropionyl]-(R)-(−)-nipecotyl}-(O-benzyl-L-aspartyl)-L-phenylalanyl-15-aza-3,6,9,12-tetraoxa-pentadecanoate (32)

Compound 29 (0.17 g, 0.42 mmol) and crude 10 (0.25 g, max. 0.38 mmol) were dissolved in DCM (5 mL). HOBt (59 mg, 0.46 mmol), EDC (94 mg, 0.49 mmol) and NMM (88 μL, 0.63 mmol) were subsequently added and the solution was allowed to stir overnight. The reaction mixture was diluted with EtOAc (10 mL) and rinsed with sat. aq. NaHCO$_3$ (2×5 mL), 5% aq. citric acid (5 mL) and H$_2$O (5 mL). The organic phase was dried (MgSO$_4$) and concentrated under reduced pressure. Purification was effected by silica gel (5 g) column chromatography (eluent: DCM/MeOH, 1/0-→95/5, v/v), to give compound 32 as a colorless oil (0.24 g, 60%). Rf 0.3 (DCM/MeOH, 95/5, v/v).

{N-3-[4-(N-benzyloxycarbonyl)-piperidinepropionyl]-(R)-(−)-nipecotyl}-(O-benzyl-L-aspartyl)-L-phenylalanyl-15-aza-3,6,9,12-tetraoxa-pentadecanoic acid (33)

Compound 32 (0.20 g, 0.19 mmol) was deprotected and purified as described earlier for the synthesis of compound 31. Yield 50 mg (30%).

tert-Butyl{N-3-[4-(N-benzyloxycarbonyl)-piperidinepropionyl]-(R)-(−)-nipecotyl}-(O-benzyl-L-aspartate (34)

To a stirred mixture of compound 29 (0.69 g, 1.72 mmol) and Asp$^{Bn}$-O-t-Bu ester (0.54 g, 1.72 mmol) in DCM (5 mL) was added TBTU (0.58 g, 1.80 mmol) and DiPEA (0.90 mL, 5.4 mmol). After 2 h the reaction mixture was diluted with EtOAc (10 mL) and washed with sat. aq. NaHCO$_3$ (2×5 mL), 5% aq. citric acid (5 mL) and H$_2$O (5 mL). The organic phase was dried over MgSO$_4$ and concentrated under reduced pressure. Silica gel (25 g) column chromatography (eluent: EtOAc/heptane, 1/2-→1/0, v/v) afforded pure compound 34 as a light yellow oil (0.84 g, 73%). Rf 0.6 (EtOAc).

tert-Butyl N-{[N-3-(4-piperidinepropionyl)-(R)-(−)-nipecotyl]-L-aspartyl}-15-aza-3,6,9,12-tetraoxa-pentadecanoate (VII)

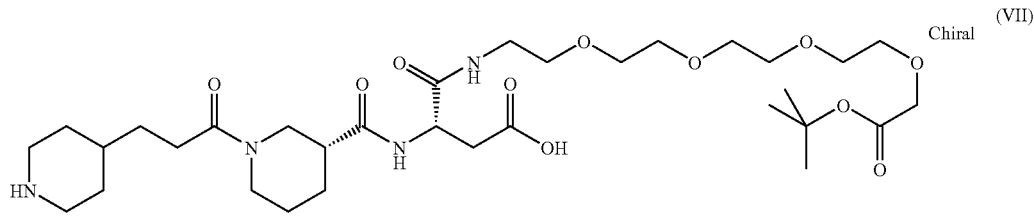

Compound 31 (35 mg, 39 μmol) was deprotected by catalytic hydrogenation over 10% Pd/C (30 mg) in a mixture of EtOH (5 mL) and H$_2$O (1 mL). After 16 h, the mixture was filtered over two layers of Whatman GF/C filter and concentrated. Compound VII was isolated as a white foam after lyophilization in a yield of 24 mg (92%). ESI-MS: 673 [M+H]$^+$.

tert-Butyl N-{[N-3-(4-piperidinepropionyl)-(R)-(−)-nipecotyl]-L-aspartyl-L-phenylalanyl}-15-aza-3,6,9,12-tetraoxa-pentadecanoate (IX)

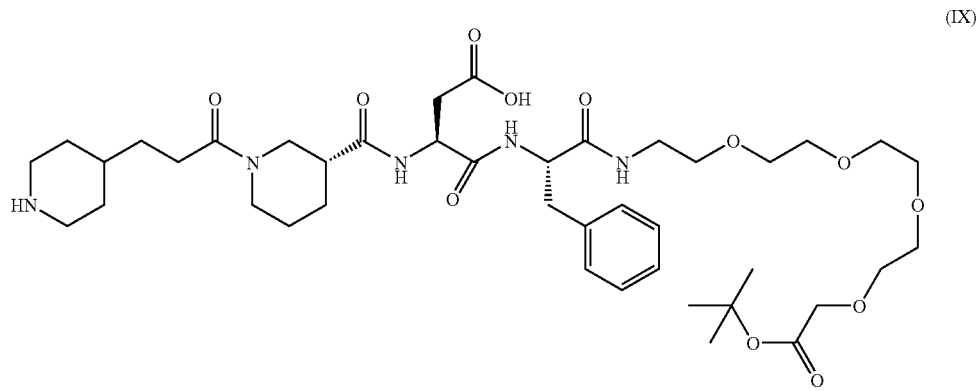

Compound 32 (45 mg, 43 μmol) was deprotected as described earlier for the synthesis of compound VII. Preparative HPLC and lyophilization afforded pure IX in a yield of 8.8 mg (26%). ESI-MS: 820 [M+H]$^+$.

1 {N-3-[4-piperidinepropionyl]-(R)-(−)-nipecotyl}-L-aspartate (VI)

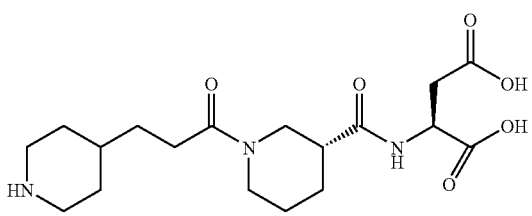

(VI)

Compound 34 (47 mg, 71 µmol) was deprotected by stirring in a mixture of DCM (5 mL) and TFA (5 mL). After 5 h the mixture was concentrated and repeatedly evaporated on toluene (3×5 mL). The crude intermediate exposed to catalytic hydrogenation over 10% Pd/C (30 mg) in a mixture of 1,4-dioxane (5 mL) and H$_2$O (5 mL). After 3 h, the mixture was filtered over two layers of Whatman GF/C filter, which were subsequently rinsed with MeOH. The filtrate was concentrated and purified by preparative HPLC to give pure compound VI as a white foam after lyophilization in a total yield of 9.8 mg (39%). ESI-MS: 384 [M+H]$^+$.

Methyl O-2,3-di-O-methyl-4-O-{[N-3-(4-piperidinepropionyl)-(R)-(−)-nipecotyl-(L)-aspartyl]-(15-aza-3,6,9,12-tetraoxa-pentadecanoyl)-(1-aza-4,7,10-trioxadodecyl)}-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (VIII)

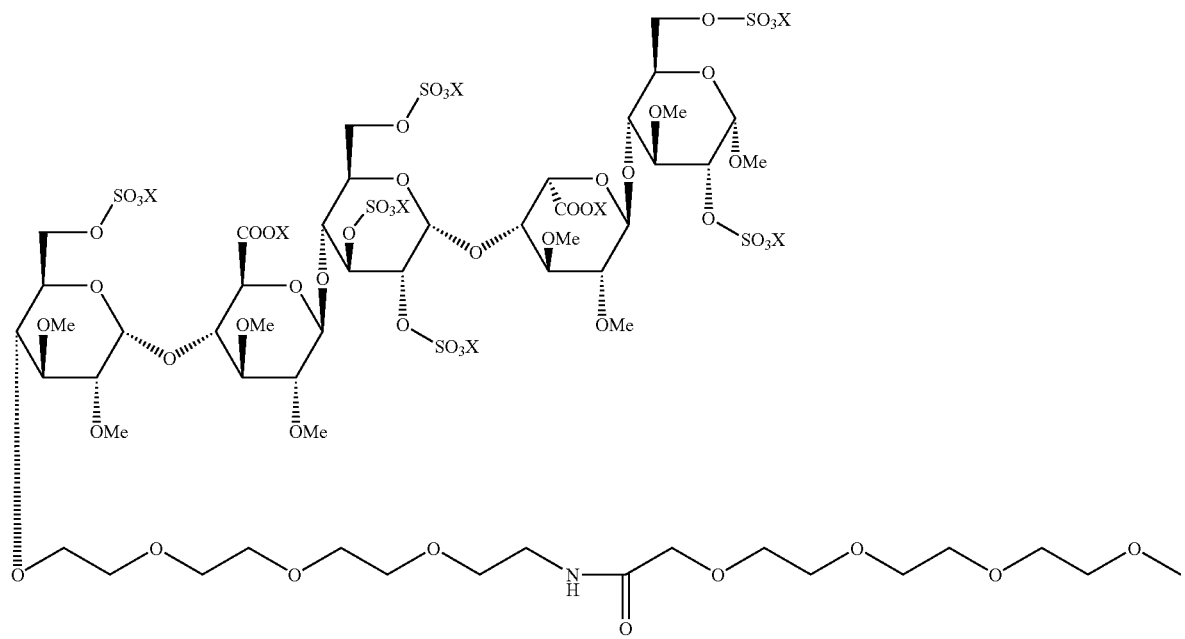

(VIII)

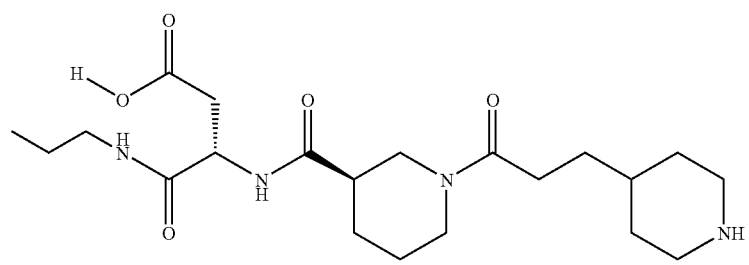

X = Na$^+$

Conjugation of carboxylic acid derivative 31 (51 mg, 59 μmol) to pentasaccharide derivative 63 (105 mg, 56 μmol), subsequent deprotection of the crude product and purification was executed as described in the general procedure. Compound VIII was obtained in pure form after lyophilization. Yield 101 mg (76% over the two steps). $^1$H-NMR (D$_2$O, 600 MHz, HH-COSY, mixture of rotamers): δ 5.39 (d, 1H, H-1 ring D), 5.31 (bs, 1H, H-1 ring F), 5.00 (d, 1H), 4.95 (bs, 1H), 4.61 (bs, 1H), 4.59 (d, 1H), 4.50 (m, 1H), 4.34 (d, 1H), 4.27-4.20 (m, 7H), 4.19-4.15 (m, 2H), 4.10-4.03 (m, 3H), 4.02 (s, 2H CH$_2$ Ac spacer), 3.92 (ddd, 1H), 3.88 (ddd, 1H), 3.86-3.75 (m, 7H), 3.71 (dd, 1H), 3.69-3.52 (m, 38H), 3.49-3.43 (m, 14H), 3.40-3.30 (m, 12H), 3.26-3.11 (m, 4H), 2.96-2.89 (m, 3H), 2.77 (m, 1H), 2.68 (m, 1H).

ESI-MS: Calculated: 2397.4; found: m/z 1221.6 [M+2Na]$^{2+}$, 1210.6 [M+H+Na]$^{2+}$, 1199.6 [M+2H]$^{2+}$, 822.1 [M+3Na]$^{3+}$, 814.8 [M+2H+Na]$^{3+}$, 807.4 [M+H+2Na]$^{3+}$, 1175.7 [M−2Na]$^{2−}$, 1164.7 [M−3Na+H]$^{2−}$, 1153.8 [M−4Na+2H]$^{2−}$, 776.2 [M−3Na]$^{3−}$, 768.9 [M−4Na+H]$^{3−}$, 761.5 [M−3Na+H]$^{3−}$, 570.9 [M−5Na+H]$^{4−}$, 576.4 [M−4Na]$^{2−}$, 456.5 [M−5Na]$^{5−}$.

Methyl O-2,3-di-O-methyl-4-O-{[N-3-(4-piperidinepropionyl)-(R)-(−)-nipecotyl-(L)-aspartyl-(L)-phenylalanyl]-(15-aza-3,6,9,12-tetraoxa-pentadecanoyl)-(1-aza-4,7,10-trioxadodecyl)}-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (X)

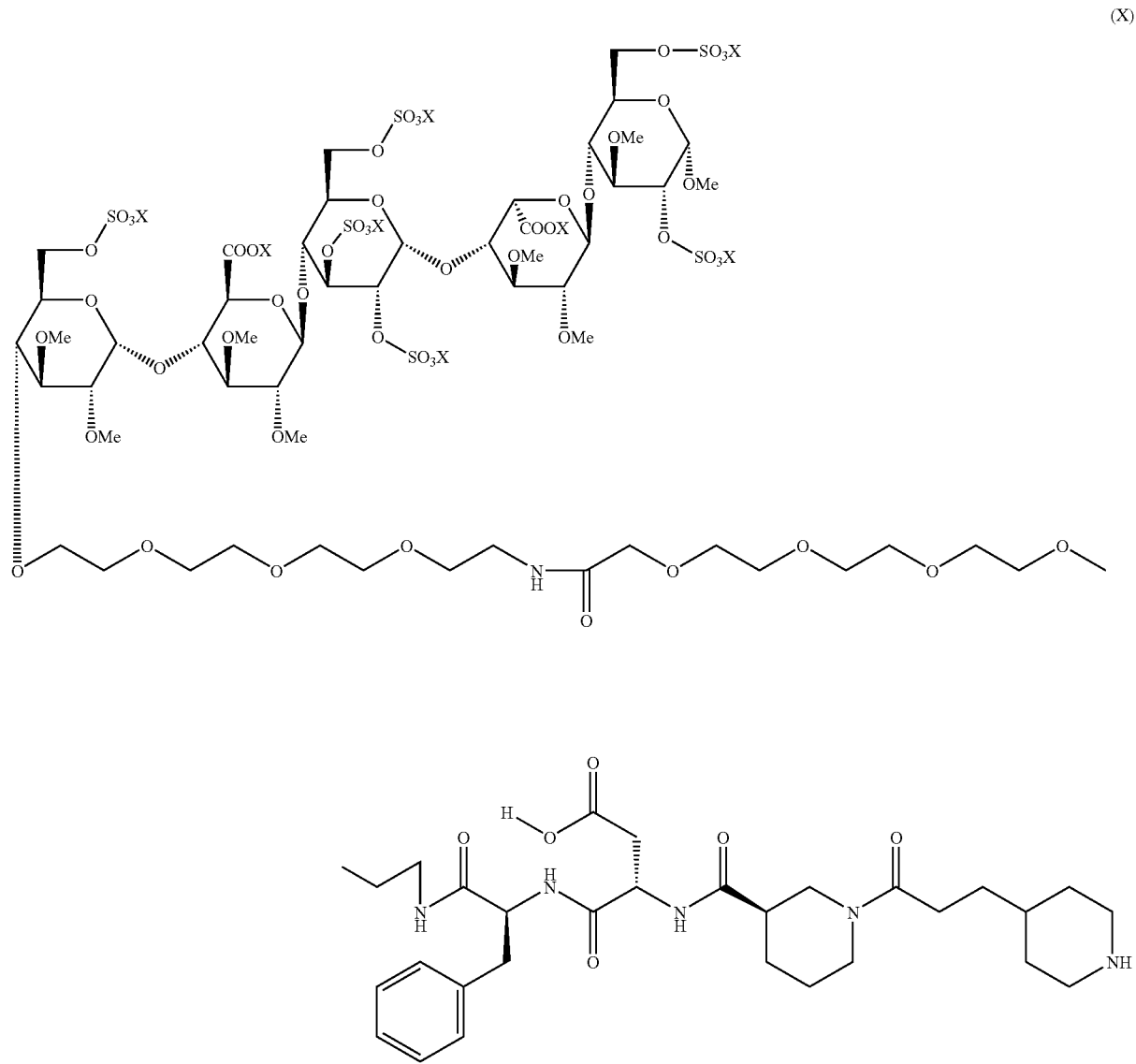

X = Na$^+$

Compound 33 (32.4 mg, 32.8 μmol) was conjugated to pentasaccharide 63 (56.0 mg, 31.2 μmol), deprotected and purified according to the general procedure to give product X as a white powder. Yield 49 mg (62% over the two steps).

$^1$H-NMR (D$_2$O, 600 MHz, HH-COSY, 1:1 mixture of rotamers): δ 7.32-7.19 (m, 5H, H-arom Phe), 5.39 (d, 1H, H-1 ring D), 5.29 (d, 1H, H-1 ring F), 4.99 (d, 1H), 4.93 (bs, 1H), 4.59 (d, 1H), 4.53 (s, 1H), 4.50-4.43 (m, 3H), 4.33 (d, 1H), 4.26-4.15 (m, 8H), 4.13-4.08 (m, 3H), 4.06-4.02 (d, 1H), 3.98 (d, 1H CH$_2$ Ac spacer), 3.94-3.78 (m, 9H), 3.74 (bs, 1H), 3.68-3.52 (m, 38H), 3.50-3.42 (m, 14H), 3.38-3.30 (m, 12H), 3.27-2.85 (m, 6H), 2.80-2.70 (m, 2H).

ESI-MS: Calculated: 2546.4; found: m/z 1273.2 [M+2H]$^{2+}$, 1284.2 [M+H+Na]$^{2+}$, 1295.2 [M+2Na]$^{2+}$, 856.5 [M+2H+Na]$^{3+}$, 863.8 [M+H+2Na]$^{3+}$, 871.1 [M+3Na]$^{3+}$, 1238.3 [M+H−3Na]$^{2-}$, 1227.3 [M+2H−4Na]$^{2-}$, 1216.3 [M+3H−5Na]$^{2-}$, 825.2 [M−3Na]$^{3-}$, 817.9 [M−4Na+H]$^{3-}$, 810.5 [M−5Na+2H]$^{3-}$, 803.2 [M−6Na+3H]$^{3-}$, 613.1 [M−4Na]$^{4-}$, 607.7 [M−5Na+H]$^{4-}$, 485.9 [M−5Na]$^{5-}$, 401.1 [M−6Na]$^{6-}$.

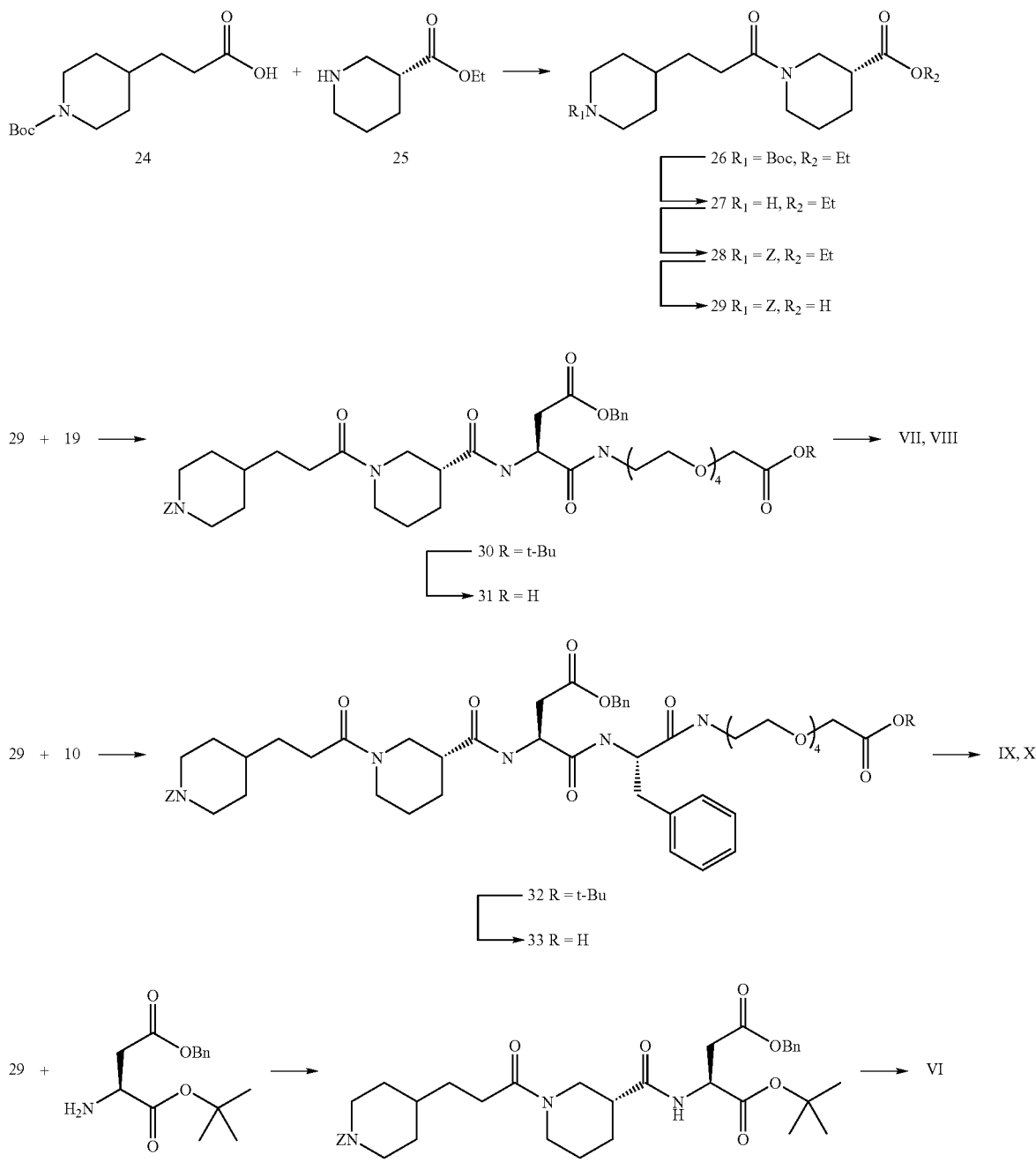

Scheme 3. Synthesis of VI, VII and IX

Scheme 4

N-(4-[1,2,4-Oxadiazol-5-onyl]-phenyl-succinamyl-O-benzyl-L-aspartate (36)

To a stirred solution of compound 17 (1.0 g) in DMF (35 mL), under a $N_2$ atmosphere, NMM (351 µL) was added followed by isobutylchloroformate (440 µL). After 5 minutes Asp(Bn)(t-Bu) (1.12 g) was added followed by DiPEA (586 µl) and DMAP (7.8 mg). After 1 h $H_2O$ was added and the mixture was extracted with EtOAc (twice). The organic layer was washed with a sat. NaCl-solution, dried on $MgSO_4$ and concentrated under reduced pressure. Toluene was added, after which product 35 precipitated. Heptane was added and the product was filtered of in a 55% yield. Rf=0.5 (DCM/MeOH/AcOH 9:1:0,1)

To 35 (843 mg) a mixture of DCM and TFA (40 mL, 1:1, v/v) was added and stirred for 3 hours. Then the mixture was concentrated after addition of toluene to give 36 in quantitative yield. Rf 0.2 (Tol/EtOH 8:2, v/v)

N-Allyloxycarbonyl-L-tyrosine (38)

To a stirred solution of tyrosine (10 g) in 4N aq. sodium hydroxide (30 mL) cooled in an ice bath was slowly added allyl chloroformate (6.4 mL) in a period of 20 minutes. Ten minutes after completion of the addition the ice bath was removed and 4N aq. sodium hydroxide (30 mL) and $H_2O$ (5mL) were added. After two hours at RT MeOH (60 mL) was added. After an additional two hours the reaction mixture was extracted with $Et_2O$. The aq. mixture was cooled in an ice bath, acidified to pH 2-3 using 36-38% hydrochloric acid and extracted with EtOAc. De organic extract was dried ($Na_2SO_4$) and concentrated under reduced pressure to give Alloc-Tyr-OH (38) as an oil (14.5 g, 88%). Rf 0.35 (DCM/MeOH/AcOH, 89/10/1, v/v/v).

N-Allyloxycarbonyl-4-O-benzyl-L-tyrosine (39)

Alloc-Tyr-OH (38, 5.5 g) was dissolved in DMF (40 mL) and half the volume of DMF was removed under reduced pressure. The residue was cooled at 0° C. under a $N_2$ atmosphere and sodium hydride (60% disperse, 1.9 g) was added in small portions. The suspension was stirred for one hour at 0° C. Then benzyl bromide (1.88 mL) in DMF (5 mL) was added. After one hour at RT 2N hydrochloric acid (7 mL) was added and the mixture concentrated under reduced pressure. To the residue $H_2O$ (50 mL) was added, the pH was adjusted to nine using 2N aq. sodium hydroxide and washed with a mixture of toluene and EtOAc. EtOAc was added and the mixture acidified to pH 3 using 2N hydrochloric acid. The organic layer was separated, dried ($Na_2SO_4$) and concentrated. The residue was purified using silica gel column chromatography (DCM/MeOH/AcOH, 89/10/1, v/v/v). The product from the column was dissolved in EtOAc, washed with $H_2O$, dried ($Na_2SO_4$) and concentrated to give compound 39 (4.66 g, 77%). Rf 0.5 (DCM/MeOH/AcOH, 89/10/1, v/v/v).

tert-Butyl(N-allyloxycarbonyl-4-O-benzyl-L-tyrosyl)-15-aza-3,6,9,12-tetraoxa-pentadecanoate (40)

To a stirred solution of alloc-Tyr(Bn)-OH (39, 0.61 g) and tert-butyl 15-amino-3,6,9,12-tetraoxa-tetradecanoate (6) (0.54 g) in THF (2 mL) was added TBTU (0.7 g) and NMM (0.38 mL). After 16 hours tert-butyl 15-amino-3,6,9,12-tetraoxa-pentadecanoate (6) (0.18 g), TBTU (0.1 g) were added and the pH adjusted to 7 (wet pH-paper) using NMM. After 3 days the reaction mixture was filtered and the filtrate concentrated under reduced pressure. The residue was purified using silica gel column chromatography (EtOAc/heptane/EtOH, 65/33/2 to 50/0/1, v/v/v) to give the title compound 40 (0.7 g, 67%). Rf 0.25 (EtOAc/heptane/EtOH, 66/33/1, v/v/v).

tert-Butyl 15-N-(4-O-benzyl-L-tyrosyl)-15-aza-3,6,9,12-tetraoxa-pentadecanoate (41)

To a stirred solution of compound 40 (0.43 g) in DCM (15 mL) was added $H_2O$ (75 µL), tributyltin hydride (0.4 mL) and $PdCl_2(PPh_3)_2$ (12 mg). The reaction was monitored by TLC (EtOAc/ethanol, 25/1, v/v). After completion of the reaction the reaction mixture was cooled at 0° C., $H_2O$ (10 mL) added and acidified to pH 4 using 2 N hydrochloric acid. The organic layer separated, dried ($Na_2SO_4$) and concentrated under reduced pressure. The residue was purified using silica gel column chromatography (gradient of DCM/MeOH, 95/5 to DCM/MeOH/N-methyl morpholine, 450/50/3) to give the title compound 41 (0.36 g, 78%). Rf 0.4 (DCM/MeOH, 10/1, v/v).

15-N-{4-[1,2,4-Oxadiazol-5-onyl]-phenyl-succinamyl-(O-benzyl-L-aspartyl)-(4-O-benzyl-L-tyrosyl)}-15-aza-3,6,9,12-tetraoxa-pentadecanoate (43)

Compound 41 (360 mg, 0.49 mmol) and 36 (241 mg, 0.5 mmol) were dissolved in THF (5 mL). To this mixture, NMM (108 µl, 0.98 mmol) was added followed by TBTU. The mixture was allowed to stir overnight. The solution was filtered on a PVDF (0.45 µm) filter. Purification was effected by silica gel column chromatography (eluent: DCM→DCM/MeOH, 95/5, v/v), to give compound 42 as an oil (560 mg, 100%). Rf 0.5 (DCM/MeOH, 9/1, v/v). Hydrolysis of the compound was carried out as described for the preparation of compound 12. Purification was carried out by silica gel column chromatography (DCM/MeOH/AcOH, 90/10/3, v/v/v), to give compound 43 (185 mg, 39%). $^1$H-NMR (MeOD, 400 MHz): 7.70 (AB, 4H, $H_{arom}$ benzamidine), 7.32 (m, 10H, Bn), 7.12 (d, 2H, Tyr), 6.88 (d, 2H, Tyr), 5.10 (d, 2H, $CH_2$ Bn), 5.00 (s, 2H, $CH_2$ Benzyl), 4.67 (m, 1H), 4.48 (m, 1H), 4.06 (s, 2H), 3.61 (m, 10H), 3.52 (m, 2H), 3.41 (m, 2H), 3.32 (m, 2H), 3.10-2.40 (m, 8H).

Methyl O-2,3-di-O-methyl-4-O-<12-[15-{N-(4-benzamidinyl)-succinamyl-L-aspartyl-L-tyrosyl)-15-aza-3,6,9,12-tetraoxa-pentadecanoyl}]-12-aza-3,6,9-trioxa-dodecyl>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (XI)

The conjugation of compound 43 (62.2 mg) with pentasaccharide 63 (110 mg), followed by deprotection and purification was carried out as outlined in the general procedure.

Yield 22 mg (14% over the 2 steps). $^1$H-NMR (D$_2$O, 600 MHz, HH-COSY): δ 3.54-3.30 (8×s, 34H, 8×OMe); ring D: 5.28 (d, 1H, H1), 4.14 (m, 1H, H6a), 3.97 (m, 1H, H6b), 3.72 (m, 1H, H5), 3.37 (m, 1H, H3), 3.24 (m, 1H, H4), 3.12 (m, 1H, H2); ring E: 4.50 (d, 1H, H1), 3.73 (m, 3H, H3,4,5), 3.16 (m, 1H, H2); ring F: 5.16 (d, 1H, H1), 4.39 (m, 2H, H3,4), 4.24 (d, 1H, H6a), 4.14 (m, 1H, H6b), 4.00 (m, 1H, H2), 3.97 (m, 1H, H5); ring G: 4.84 (bs, 1H, H1), 3.97 (m, 1H, H4), 3.66 (m, 2H, H2,3); ring H: 4.91 (d, 1H, H1), 4.14 (m, 2H, H2,6a), 4.08 (m, 1H, H6b), 3.84 (m, 1H, H5), 3.51 (m, 1H, H3); spacer: 3.88 (s, 2H, C(O)CH$_2$O), 3.54-3.24 (m,32H) peptide: 7.59 (d, 2H, H$_{arom}$ benzamidine), 7.53 (d, 2H, H$_{arom}$ benzamidine), 6.84 (d, 2H, H$_{arom}$ Tyr), 6.63 (d, 2H, H$_{arom}$ Tyr), 4.38 (dd, 1H, CH Asp), 4.21 (t, 1H, CH Tyr), 2.70 (m, 2H, CH$_2$ Tyr), 2.47(m, 1H, CH$_2$ Asp), 2.30 (dd, 1H, CH$_2$ Asp), 2.74-2.40 (m, 4H, succinyl).

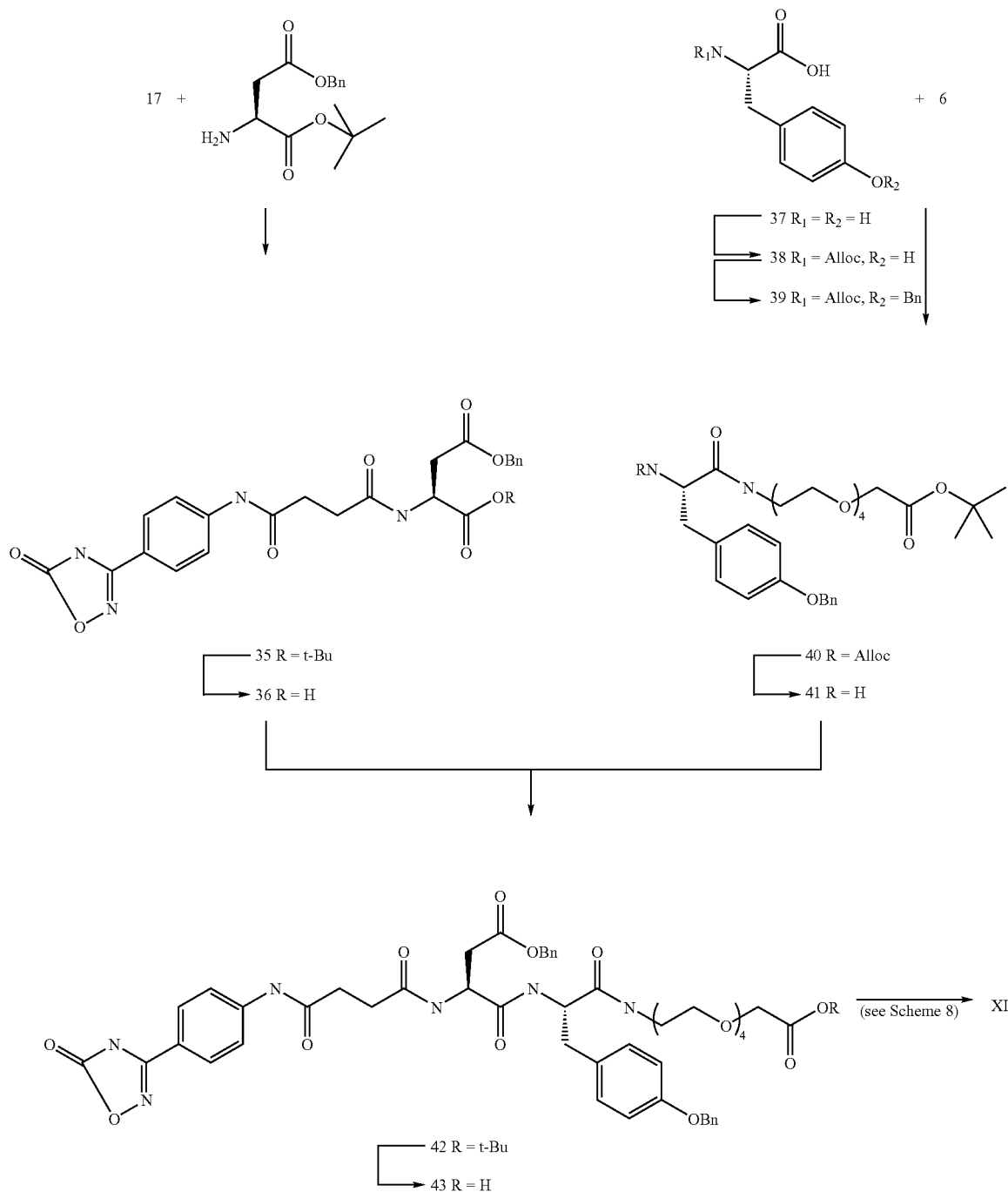

Scheme 4. Synthesis of XI

Scheme 5 tert-Butyl 15-hydroxy-3,6,9,12-tetraoxa-tetradecanoate (44)

To a stirred mixture of tetraethylene glycol (40 mL) and THF (15 mL) was added potassium tert-butoxide (2.8 g). The reaction mixture was heated at 40 to 50° C. until a clear solution was obtained. This solution was cooled to 0° C. and tert-butyl bromoacetate (4 ML, 246 mmol) was added in one portion. The cooling bath was removed and the reaction mixture was stirred at RT for two hours. It was diluted with EtOAc and washed with brine twice. Both brine layers were extracted with EtOAc four times. The combined organic layers were dried ($Na_2SO_4$) and concentrated under reduced pressure to give compound 44 (4.66 g). $^1$H-NMR ($CDCl_3$, 400 MHz): δ 4.03 (s, 2H), 3.60-3.76 (m, 16H), 1.47 (s, 9H).

tert-Butyl 14-(toluene-4-sulfonyloxy)-3,6,9,12-tetraoxa-tetradecanoate (45)

To a stirred mixture of compound 44 (4.66 g) in DCM (30 mL) at 0° C. were added NMM (2 mL) and p-toluenesulfonyl chloride (3.2 g). The cooling was removed and the reaction mixture was stirred at RT for 18 hours. Brine was added and the mixture was extracted three times with DCM. The combined organic layers were dried ($Na_2SO_4$) and concentrated under reduced pressure to give an oil (7.4 g) that still contained starting material. This oil was again dissolved in DCM (30 mL) and NMM (2 mL) and p-toluenesulfonyl chloride (3.2 g) were added to the stirred solution at 0° C. After 2 days at RT brine was added and the mixture was extracted three times with DCM. The combined organic layers were dried ($Na_2SO_4$) and concentrated under reduced pressure. The crude product was purified using silica gel column chromatography (EtOAc/heptanes, 1/1, v/v) to give compound 45 (4.6 g, 66%). Rf 0.15 (EtOAc/heptanes 1/1, v/v).

tert-Butyl 14-[4-O-(N-tert-butyloxycarbonyl-L-tyrosine benzyl ester)]-3,6,9,12-tetraoxa-tetradecanoate (47)

A stirred mixture of Boc-Tyr-OBn (46, 0.6 g), compound 45 (1.0 g), cesium carbonate (0.82 g) and sodium iodide (0.12 g) in DMF (30 mL) was heated at 70° C. under a $N_2$ atmosphere. After 20 hours the reaction mixture was allowed to cool to RT and brine was added. The mixture was extracted with EtOAc (four times). The combined organic layers were dried ($Na_2SO_4$) and concentrated under reduced pressure. The crude product was purified using silica gel column chromatography (EtOAc/toluene, gradient 1/2 to 1/1, v/v) to give compound 47 (0.92 g, 80%). Rf 0.15 (EtOAc/heptanes, 1/1, v/v).

tert-Butyl 14-<4-O-{4-[1,2,4-oxadiazol-5-onyl]-phenyl-succinamyl-(O-benzyl-L-aspartyl)-L-tyrosine benzyl ester}>-3,6,9,12-tetraoxa-tetradecanoate (49)

To a stirred mixture of compound 47 (0.42 g) in tert-butyl acetate (4 mL) at 0° C. was added a solution of 4 N hydrogen chloride in dioxane (2 mL). After 2 hours sulfuric acid (0.04 mL) was added and after half an hour an additional portion sulfuric acid (0.04 ML) was added. After another half an hour a sat. aq. solution of sodium hydrogencarbonate was added and the mixture was extracted four times with EtOAc. The combined organic layers were dried ($Na_2SO_4$) and concentrated under reduced pressure to give compound 48 (0.14 g).

This compound was dissolved in THF (2 mL) and to this stirred solution was added compound 36 (0.11 g), TBTU (84 mg) and 30 μL NMM. After two hours the reaction mixture was concentrated under reduced pressure. The residue was purified using silica gel column chromatography (EtOAc/EtOH, gradient 1/0 to 9/1, v/v) to give compound 49 (90 mg, 36%). Rf 0.5 (EtOAc/EtOH 9/1, v/v).

14-<4-O-{4-[1,2,4-Oxadiazol-5-onyl]-phenyl-succinamyl-(O-benzyl-L-aspartyl)-O-benzyl-L-tyrosyl}-3,6,9,12-tetraoxa-tetradecanoate (50)

Compound 49 (90 mg) was dissolved in dioxane and concentrated under reduced pressure. The residue was dissolved in DCM (1 mL) and TFA (1 mL) was added. After two hours dioxane (5 mL) was added and the mixture was concentrated under reduced pressure. The residue was dissolved in acetonitrile and concentrated under reduced pressure. The residue was purified using HPLC:column LUNA 10 u C18(2) 250×50 mm, flow 50 mL/min, gradient 3% 0.1 N TFA in $H_2O$, 47% acetonitril and 50% $H_2O$/acetonitril (10/1, v/v) to 3% 0.1 N TFA in $H_2O$, 90% acetonitrile and 7% $H_2O$/acetonitril (10/1 v/v) in 30 minutes to give compound 50 (73 mg, 85%). MS (EI): m/z 970 [M+H]$^+$.

Methyl O-2,3-di-O-methyl-4-O-<12-N-[14-{N-(4-benzamidinyl)-succinamyl-L-aspartyl-4-O-L-tyrosyl)]-3,6,9,12-tetraoxa-tetradecanoyl}-12-aza-3,6,9-trioxa-dodecyl>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (XII)

The product was obtained by conjugation of compound 50 (40.3 mg, 41.5 μmol) to pentasaccharide 63 (71.1 mg, 39.5 μmol), followed by purification and deprotection, according to the general procedure. The product was obtained as a white fluffy solid, yield 63.5 mg (60%, 2 steps). $^1$H-NMR ($D_2O$, 600 MHz, HH-COSY): δ 3.43-3.32 (8xs, 34H, 8×OMe); ring D: 5.36 (d, 1H, H1), 4.21 (m, 1H, H6a), 4.05 (d, 1H, H6b), 3.77 (m, 1H, H5), 3.44 (m, 1H, H3), 3.31 (m, 1H, H4), 3.19 (dd, 1H, H2); ring E: 4.58 (d, 1H, H1), 3.79 (m, 1H, H4), 3.67 (m, 1H, H5), 3.44 (m, 1H, H3), 3.16 (m, 1H, H2); ring F: 5.28 (d, 1H, H1), 4.48 (m, 1H, H3), 4.32 (d, 1H, H6a), 4.18 (m, 1H, H2), 4.15 (m, 1H, H6b), 4.07 (m, 1H, H5), 3.86 (t, 1H, H4); ring G: 4.92 (bs, 1H, H1), 4.07 (m, 1H, H4), 3.91 (dd, 1H, H3), 3.31 (m, 1H, H2), 3.18 (m, 1H, H5); ring H: 4.98 (d, 1H, H1), 4.23 (dd, 1H, H2), 4.22 (m, 1H, H6a), 4.17 (m, 1H, H6b), 3.93 (ddd, 1H, H5), 3.59 (m, 1H, H4), 3.57 (m, 1H, H3); spacer: 3.96 (s, 2H, C(O)CH$_2$O), 3.61-3.51 (m, 26H, 13×CH$_2$O), 3.38-3.30 (m, 4H, OCH$_2$CH$_2$NHCH(O)CH$_2$, OCH$_2$CH$_2$NHC(O)-Phe), 3.19 (m, 1H, OCH$_{2a}$CH$_2$NHC(O)-Phe), 3.12 (m, 1H, OCH$_{2b}$CH$_2$NHC(O)-Phe); peptide: 7.70 (d, 2H, H$_{arom}$ benzamidine), 7.62 (d, 2H, H$_{arom}$ benzamidine), 7.01 (d, 2H, H$_{arom}$ Tyr), 6.77 (d, 2H, H$_{arom}$ Tyr), 4.57 (dd, 1H, CH Asp), 4.28 (dd, 1H, CH Tyr), 2.87 (dAB, 2H, CH$_2$ Tyr), 2.50 (t, 2H, CH$_2$ succinyl), 2.48 (t, 2H, CH$_2$ succinyl), 2.48 (dAB, 2H, CH$_2$ Asp).

Scheme 5. Synthesis of XII.

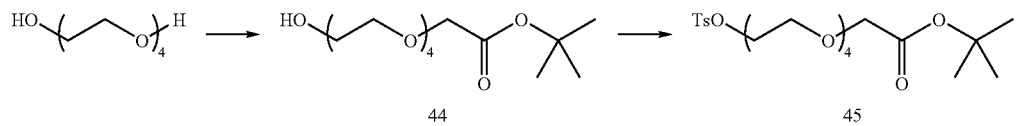

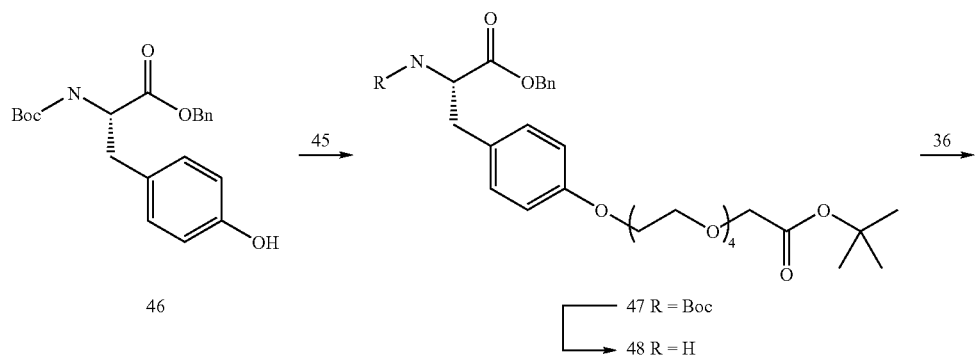

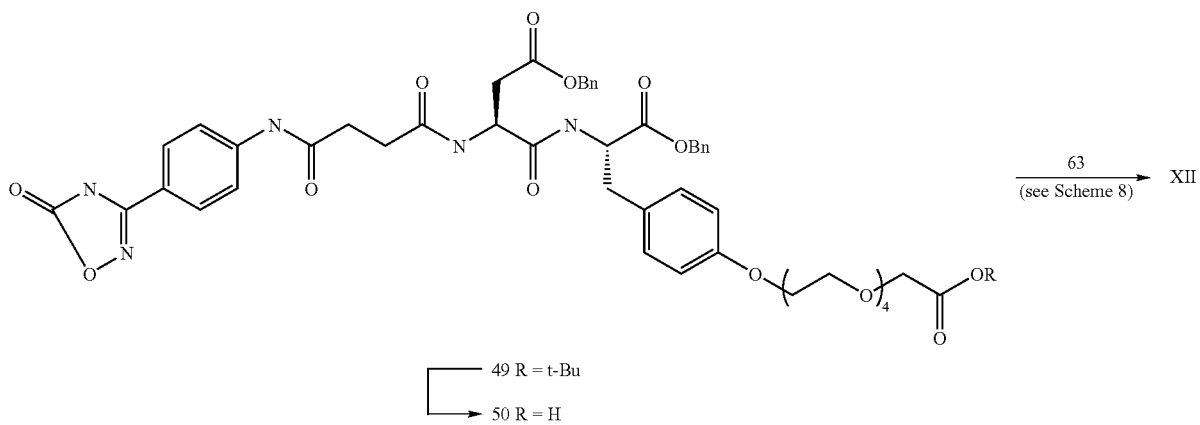

Scheme 6

Benzyl N-(3-Carboxybenzenesulfonyl)-4-O-{4-(N-benzyloxycarbonyl-4-piperidinyl)-butyl}-L-tyrosine (52)

Compound 51 (123 mg, prepared as described in *Bioorg. Med. Chem.* 2001, 29, 357-379) was dissolved in a mixture of acetonitrile and $H_2O$ (10 mL, 6/4, v/v). Potassium carbonate (381 mg) was added and the solution was cooled to 0° C. 3-Carboxybenzenesulfonyl chloride was added in portions during a period of 15 min. and the mixture was stirred for 30 min. at 0° C. and 1 h at RT. The solution was cooled to 0° C. again and another portion of 3-carboxybenzenesulfonyl chloride (102 mg) was added. After 30 min. the reaction mixture was allowed to warm to RT and stirred overnight. The mixture was acidified to pH 1 with 1N hydrochloric acid, concentrated under reduced pressure and the crude product was dissolved in EtOAc. The organic layer was washed with 1N hydrochloric acid, sat. solution of NaCl, dried ($MgSO_4$) and concentrated to give compound 52 (0.11 g, 73%). Rf 0.5 (DCM/MeOH, 9/1, v/v). MS (ESI) $M^+=729$.

Benzyl N-<3-{[14-N-(14-aza-1-carboxy-2,5,8,11-tetraoxa-tetradecyl)]-keto}-benzenesulfonyl>-4-O-{4-(N-benzyloxycarbonyl-4-piperidinyl)-butyl}-L-tyrosine (54)

Crude compound 52 (216 mg) and compound 6 (49 mg) were dissolved in DCM (5 mL). TBTU (145 mg) and NMM (82 uL) were added and the mixture was stirred overnight at RT. The mixture was diluted with EtOAc, washed with sat. $NaHCO_3$, citric acid and sat. NaCl. The combined aq. phases were extracted with ethyl acetate after which the combined organic phases were dried with $MgSO_4$ and concentrated to give 0.31 g of 68 as a brown oil. Next, crude compound 53 was stirred in a mixture of DCM (5 mL) and TFA (2.5 mL). After 4 h the mixture was concentrated. The product was purified by preparative LC/MS (C18, acetonitrile/$H_2O$, 0.01% TFA) to give 84 mg of compound 54.

Methyl O-2,3-di-O-methyl-4-O-<<12-N-<3-{[14-N-(14-aza-1-carbonyl-2,5,8,11-tetraoxa-tetradecyl)]-keto}-benzenesulfonyl>-4-O-{4-(4-piperidinyl)-butyl}-L-tyrosine>-12-aza-3,6,9-trioxa-dodecyl>>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (XIII)

Conjugation of carboxylic acid 54 (53 mg) to pentasaccharide 63 (95 mg), followed by purification and deprotection was effected according to the general procedure. Conjugate XIII was obtained as a white foam. Yield 77 mg (58% over the two steps).

$^1$H-NMR (D$_2$O, 600 MHz, HH-COSY): δ 3.43-3.32 (8×s, 34H, 8×OMe); ring D: 5.39 (d, 1H, H1), 4.22 (m, 1H, H6a), 4.04 (d, 1H, H6b), 3.79 (m, 1H, H5), 3.46 (m, 1H, H3), 3.34 (m, 1H, H4), 3.24 (dd, 1H, H2); ring E: 4.59 (d, 1H, H1), 3.82 (m, 1H, H4), 3.66 (m, 1H, H5), 3.52 (m, 1H, H3), 3.20 (m, 1H, H2); ring F: 5.28 (d, 1H, H1), 4.48 (t, 1H, H3), 4.34 (d, 1H, H6a), 4.22 (m, 1H, H2), 4.09 (m, 1H, H5), 3.85 (m, 1H, H4); ring G: 4.92 (bs, 1H, H1), 4.52 (bs, 1H, H5), 4.09 (m, 1H, H4), 3.75 (1H, m, H3), 3.35 (dd, 1H, H2); ring H: 4.99 (d, 1H, H1), 4.22 (m, 2H, H2, H6a), 4.16 (m, 1H, H6b), 3.91 (ddd, 1H, H5), 3.68 (m, 1H, H4), 3.60 (m, 1H, H3); spacer: 3.91 (s, 2H, C(O)CH$_2$O), 3.66-3.32 (m, 32H, 16×CH$_2$). peptide: 7.85 (dt, 1H, H$_{arom}$), 7.75 (t, 1H, H$_{arom}$), 7.62 (dt, 1H, H$_{arom}$), 7.43 (t, 1H, H$_{arom}$), 6.83 (d, 2H, H$_{arom}$ Tyr), 6.48 (d, 2H, H$_{arom}$ Tyr), 3.86 (m, 2H, CH$_2$O), 3.65 (m, 1H, H-1 Tyr), 3.36 (m, 2H, CH$_2$N), 2.91 (m, 2H, CH$_2$N), 1.91 (m, 2H, CH$_2$ piperidyl), 1.72 (m, 2H, CH$_2$ butyl), 1.59 (m, 1H, CH piperidyl), 1.44 (m, 2H, CH$_2$ butyl), 1.36 (m, 4H).

ESI-MS: m/z 1272.3 [M+2TEA−2H]$^{2-}$, 814.5 [M+TEA−3H]$^{3-}$, 799.1 [M−3H]$^{3-}$, 585.0 [M−4H]$^{4-}$.

Methyl O-2,3-di-O-methyl-4-O-<<12-N-<N-(3-keto-benzenesulfonyl)-4-O-{4-(4-piperidinyl)-butyl}-L-tyrosine>-12-aza-3,6,9-trioxa-dodecyl>>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (XIV)

Conjugation of carboxylic acid 52 (22.5 mg) to pentasaccharide 63 (52.6 mg), followed by purification and deprotection, was effected according to the general procedure. Conjugate XIV was obtained as a white foam. Yield 38.4 mg (58% over the two steps).

$^1$H-NMR (D$_2$O, 600 MHz, HH-COSY): δ 3.43-3.32 (8×s, 34H, 8×OMe); ring D: 5.39 (d, 1H, H1), 4.22 (m, 1H, H6a), 4.04 (d, 1H, H6b), 3.79 (m, 1H, H5), 3.46 (m, 1H, H3), 3.34 (m, 1H, H4), 3.20 (dd, 1H, H2); ring E: 4.58 (d, 1H, H1), 3.82 (m, 1H, H4), 3.66 (m, 1H, H5), 3.52 (m, 1H, H3), 3.18 (m, 1H, H2); ring F: 5.28 (d, 1H, H1), 4.49 (t, 1H, H3), 4.34 (d, 1H, H6a), 4.20 (m, 1H, H2), 4.08 (m, 1H, H5), 3.85 (m, 1H, H4); ring G: 4.94 (bs, 1H, H1), 4.54 (bs, 1H, H5), 4.08 (m, 1H, H4), 3.75 (1H, m, H3), 3.35 (dd, 1H, H2); ring H: 4.98 (d, 1H, H1), 4.22 (m, 2H, H2, H6a), 4.17 (m, 1H, H6b), 3.92 (ddd, 1H, H5), 3.68 (m, 1H, H4), 3.60 (m, 1H, H3); spacer: 3.62-3.38 (m, 16H, 8×CH$_2$). peptide: 7.83 (dt, 1H, H$_{arom}$), 7.71 (t, 1H, H$_{arom}$), 7.62 (dt, 1H, H$_{arom}$), 7.42 (t, 1H, H$_{arom}$), 6.81 (d, 2H, H$_{arom}$ Tyr), 6.46 (d, 2H, H$_{arom}$ Tyr), 3.84 (m, 2H, CH$_2$O), 3.66 (m, 1H, H-1 Tyr), 3.33 (m, 2H, CH$_2$N), 2.90 (m, 2H, CH$_2$N), 1.93 (m, 2H, CH$_2$ piperidyl), 1.72 (m, 2H, CH$_2$ butyl), 1.59 (m, 1H, CH piperidyl), 1.44 (m, 2H, CH$_2$ butyl), 1.34 (m, 4H).

ESI-MS: m/z 1155.2 [M+2TEA−2H]$^{2-}$, 736.3 [M+TEA−3H]$^{3-}$, 702.6 [M−3H]$^{3-}$.

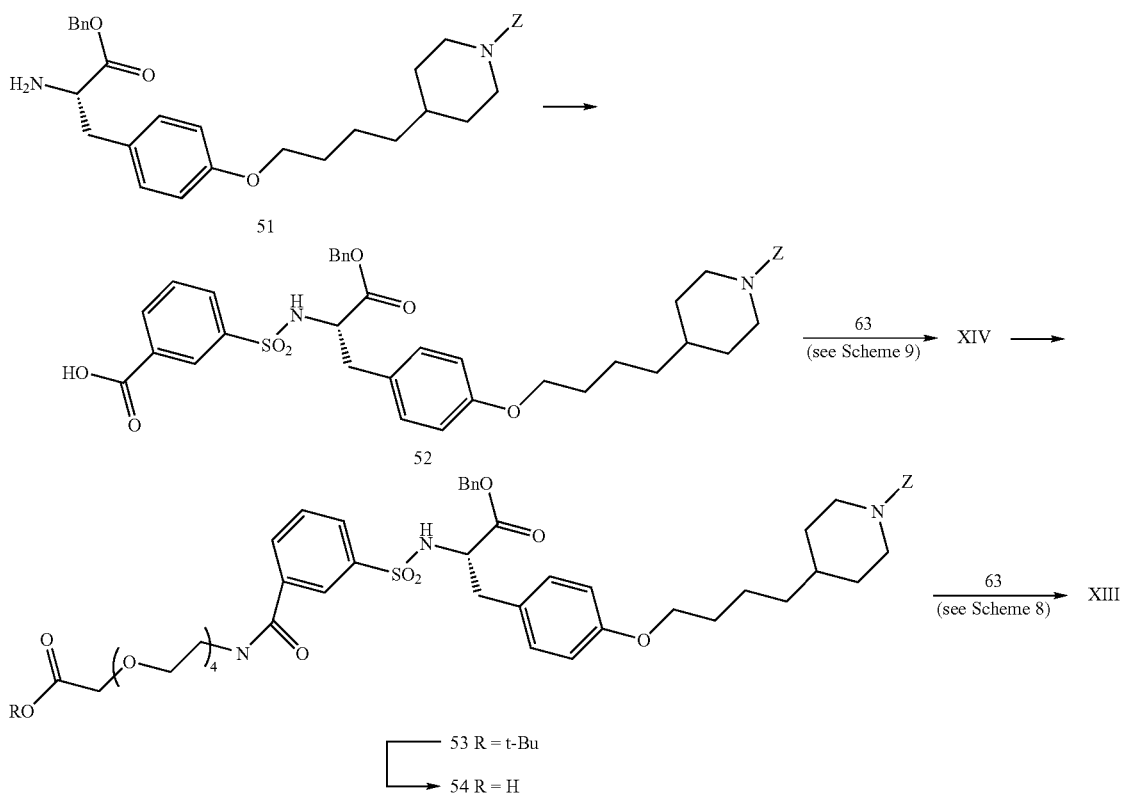

Scheme 6. Synthesis of XIII and XIV

Scheme 7 tert-Butyl 14-[4-O-(N-allyloxycarbonyl-L-tyrosyl)]-3,6,9,12-tetraoxa-tetradecanoate (55)

Compound 38 (1.0 g) was dissolved in DMF (50 mL) and 10 mL of DMF was removed under reduced pressure. The residue was cooled at 0° C. under an $N_2$ atmosphere and sodium hydride (60% disperse, 0.34 g) was added in small portions. The suspension was stirred for one hour at 0° C. Then compound 45 (1.3 g) in DMF (4 mL) was added. After 24 hours at RT the reaction mixture was concentrated under reduced pressure. To the residue $H_2O$ (50 mL) was added and the mixture was washed with EtOAc. EtOAc and solid sodium chloride was added and the mixture was acidified to pH 3 using 2N aq. hydrochloric acid. The organic layer was separated, dried ($Na_2SO_4$) and concentrated. The residue was purified using silica gel column chromatography (DCM/MeOH/AcOH, 949/50/1, v/v/v). The product from the column was dissolved in EtOAc, washed with $H_2O$, dried ($Na_2SO_4$) and concentrated to give compound 55 (0.6 g, 37%). Rf 0.4 (EtOAc/pyridine/AcOH/$H_2O$ 270/16/9/4, v/v/v/v).

Benzyl 2-[(4-piperidinyl)oxy]acetate (57)

tert-Butyl 2-[(4-piperidinyl)oxy]acetate (56) was prepared as previously described in *J. Med. Chem.* 1992, 35, 4393-4407. To compound 56 (4.3 g 20 mmol) 50 mL of DCM/TFA (1:1) was added and the solution was allowed to stir for about 30 minutes. The mixture was concentrated under reduced pressure. The crude product was dissolved in a mixture of EtOH (40 mL) and NMM (7 mL) to which was added di-tert-butyl-dicarbonate (4.8 g, 22 mmol). The mixture was allowed to stir for about 55 h. Next, the reaction mixture was concentrated under reduced pressure. To the residue 4 M NaOH (250 mL) and $Et_2O$ were added and the layers were separated after extraction. The $H_2O$ layer was acidified to pH 3 using 2N hydrochloric acid and was subsequently extracted 3 times with EtOAc. The combined organic layers were dried (magnesium sulfate) and concentrated to give 2-[4-(N-Boc-piperidinyl)oxy]acetate (2.1 g, 40%).

The latter crude product was dissolved in acetone (25 mL) and triethylamine (3.4 mL). Benzyl bromide (965 µL, 8.1 mmol) was added and the reaction mixture was allowed to stir overnight. Ice water (200 mL) and EtOAc were added. The mixture was acidified to pH 3 with 2N hydrochloric acid. The organic layer was washed with sat. $NaHCO_3$ and brine, dried ($Na_2SO_4$) and concentrated to give 760 mg of the crude product. The product was purified using silica gel column chromatography (heptane/EtOAc, 1/1, v/v) to give 418 mg (15%) of pure product. Rf 0.47 (heptane/EtOAc, 1/1, v/v). The latter product was dissolved in DCM/TFA (10 mL, 1/1, v/v) and stirred for 1 h. The reaction mixture was concentrated under reduced pressure and toluene (5 mL) was added. Dissolved in EtOAc (50 mL) and washed with sat. $NaHCO_3$. The aq. layer was extracted twice with EtOAc. The combined organic layers were dried ($Na_2SO_4$) and concentrated to give 331 mg (100%) of the title compound 57. $^1$H-NMR (MeOD, 400 MHz, HH): δ 7.37 (m, 5H, Ar), 6.00 (s, 2H), 4.17 (s, 2H), 3.56 (m, 1H), 3.16 (m, 1H), 2.76 (m, 1H), 1.98 (m, 1H) 1.63 (m, 1H).

tert-Butyl 14-{[4-O-(N-allyloxycarbonyl-L-tyrosyl)]-2-[(4-piperidinyl)oxy]acetate benzyl ester}-3,6,9,12-tetraoxa-tetradecanoate (58)

Coupling of compound (55) (400 mg, 0.72 mmol) and (57) (215 mg, 0.86 mmol) was performed as described earlier for compound 64. The product was purified by silica gel column chromatography (DCM→DCM/MeOH, 95/5, v/v) to give 587 mg (91%) of the title compound 58. Rf 0.65 (DCM/MeOH/AcOH, 95/5/0.3, v/v/v).

tert-Butyl 14-{4-O-L-tyrosyl-2-[(4-piperidinyl)oxy] acetate benzyl ester}-3,6,9,12-tetraoxa-tetradecanoate (59)

To a solution of compound 58 (587 mg, 0.66 mmol) in DCM (15 mL) was subsequently added $H_2O$ (75 µL), morpholine (115 µL, 1.32 mmol) and $PdCl_2(PPh_3)_2$. After 3 h the reaction mixture was poured in a $H_2O$/brine (1/1, v/v) mixture which was extracted with DCM. The organic layer was dried ($Na_2SO_4$) and concentrated. The residue was purified using silica gel column chromatography (DCM/MeOH, 9/1, v/v) to give 433 mg (89%) of the title compound 59. Rf 0.66 (DCM/MeOH, 9/1, v/v).

N-(4-[1,2,4-Oxadiazol-5-onyl]-benzoic acid (60)

p-Cyanobenoic acid methyl ester (5.0 g, 31 mmol) was converted into the corresponding oxadiazolinone as described for the synthesis of compound 3. The crude product (4.6 g, 20.9 mmol) was dissolved in a mixture of THF (50 mL) and MeOH (50 mL). $H_2O$ (50 mL) was added, which gave a suspension, followed by 4 N aq. NaOH (10 mL). After 6 h the organic solvents were removed by distillation under reduced pressure. The aq. layer was extracted with EtOAc/toluene (1/2, v/v), acidified with 2 N hydrochloric acid and the precipitate was filtered off. The crude product was dried at 40° C. under reduced pressure to give 4.2 g (97%) of compound 60. ESI-MS: 207 $[M+H]^+$.

tert-Butyl 14-{{N-(4-[1,2,4-Oxadiazol-5-onyl]-benzoyl}-{4-O-L-tyrosyl-2-[(4-piperidinyl)oxy]acetate benzyl ester}}-3,6,9,12-tetraoxa-tetradecanoate (61)

To a solution of compound 59 (433 mg, 0.59 mmol) and 60 (134 mg, 0.65 mmol) in DMF (6 mL), TBTU (227 mg, 0.71 mmol) and NMM (130 µL, 1.18 mmol) were added. After 16 h of stirring at RT the reaction mixture was concentrated under reduced pressure. EtOAc was added and the organic layer was washed with brine, dried ($Na_2SO_4$) and concentrated. The product was purified by HPLC (C18, ACN/$H_2O$) to give 337 mg (64%) of compound 61. ESI-MS: 891 $[M+H]^+$, 913 $[M+Na]^+$, 835 $[M-tBu+H]^-$.

14-{{N-(4-[1,2,4-Oxadiazol-5-onyl]-benzoyl}-{4-O-L-tyrosyl-2-[(4-piperidinyl)oxy]acetate benzyl ester}}-3,6,9,12-tetraoxa-tetradecanoate (62)

Hydrolysis of the t-Bu ester was carried out as previously described for the preparation of compound 12. The product was purified by HPLC (C18, ACN/$H_2O$/3% 0.1 N TFA(aq)) to give 181 mg (57%) of the desired compound 62. $^1$H-NMR (MeOD, 400 MHz): 7.91 (AB, 4H, $H_{arom}$ benzamidine), 7.35 (m, 5H, Bn), 7.19 (d, 2H, Tyr), 6.88 (dd, 2 H, Tyr), 5.24 (m, 1H, CH Tyr), 5.18 (d, 2H, $CH_2$ Bn), 4.17 (d, 2H), 4.10 (s, 2H), 4.08 (m, 2H), 3.80 (m, 2H), 3.65 (m, 14H), 3.58 (m, 1H), 3.32 (m, 2 H), 3.07 (m, 2H), 1.82-1.01 (m, 4H). ESI-MS: 835 $[M+H]^+$.

Methyl O-2,3-di-O-methyl-4-O-<[1-amino-4,7,10-trioxadodecyl]-14-{{N-(4-[1,2,4-oxadiazol-5-onyl]-benzoyl}-{4-O-L-tyrosyl-2-[(4-piperidinyl)oxy]acetate benzyl ester}}-3,6,9,12-tetraoxa-tetradecanoyl>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-3-O-methyl-2,6-di-O-sulfo-alpha-D-glucopyranoside octakis sodium salt (XV)

The conjugation of compound 62 (51.7 mg) with pentasaccharide 63 (106 mg), followed by deprotection and purification was carried out as described in the general procedure. Yield 127 mg (87% over the 2 steps).

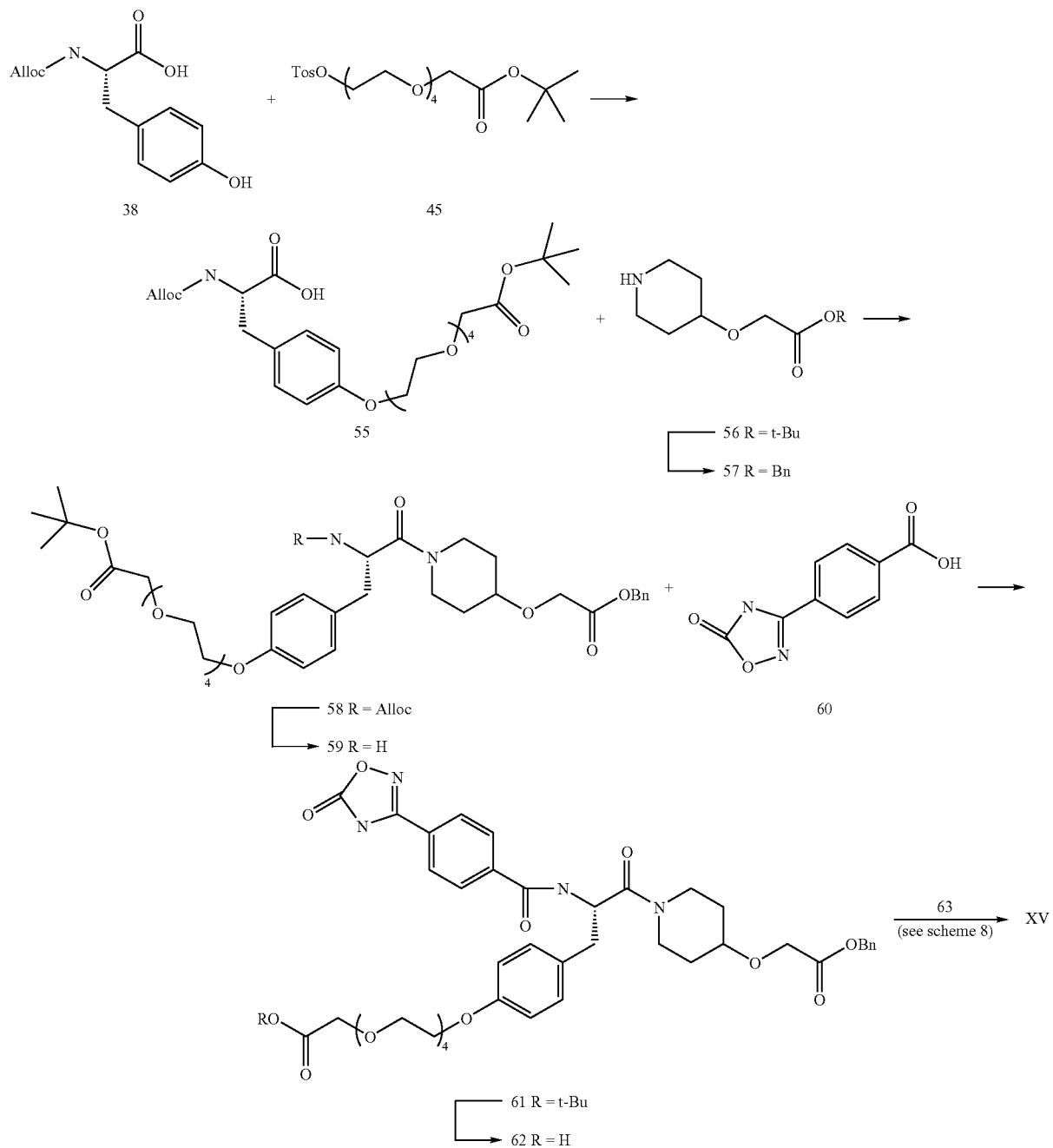

Scheme 7. Synthesis of XV.

-continued
Scheme 8. Synthesis of II, V, VIII, X-XIII, XV, XVI
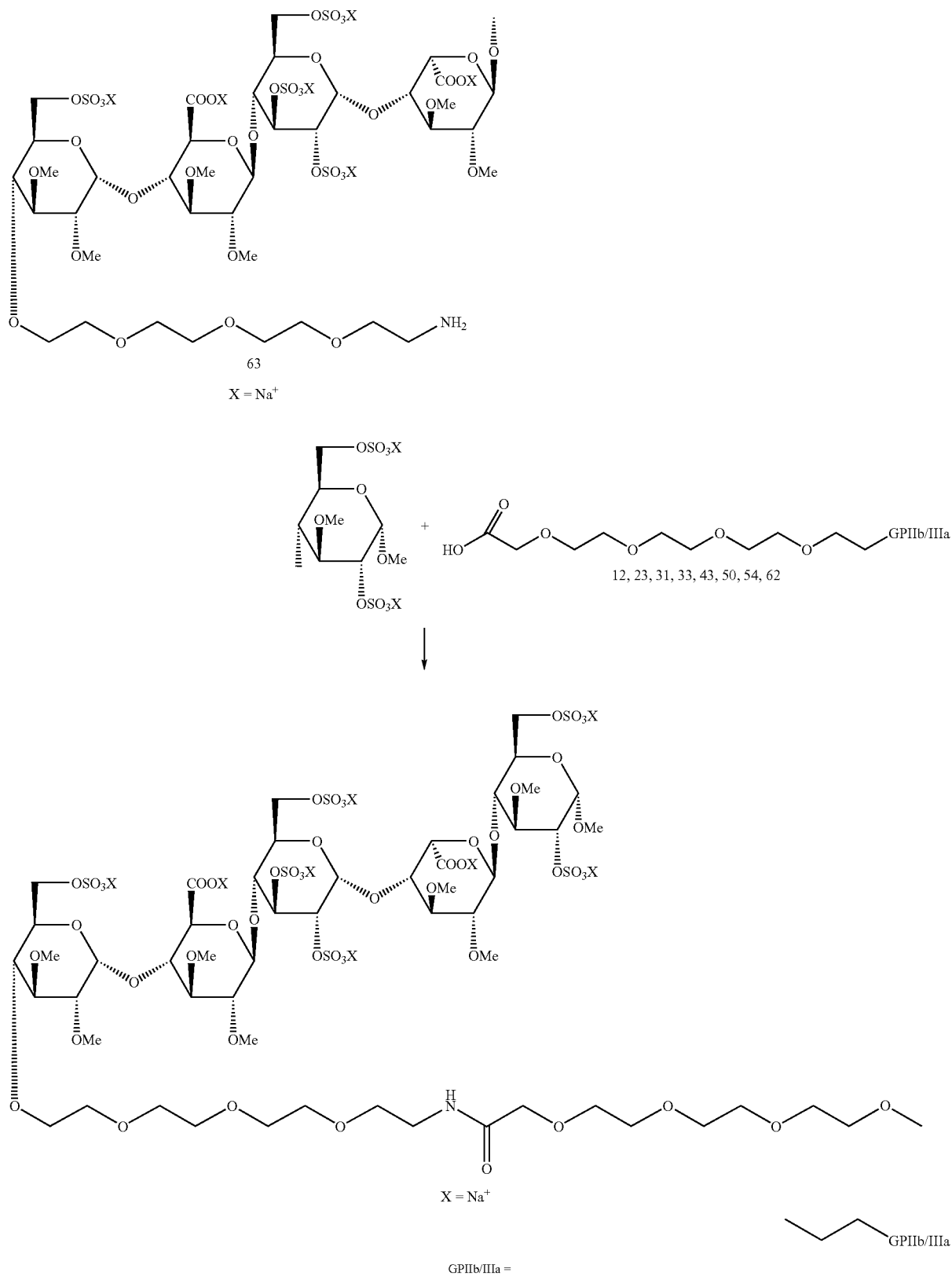

-continued
II:
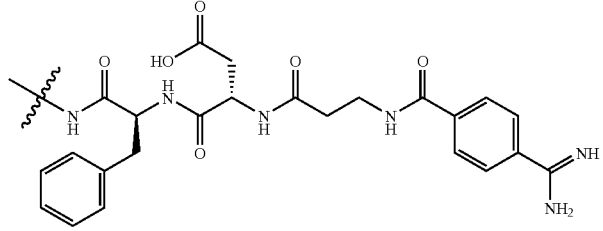
VIII:
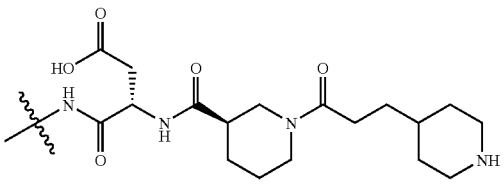
V:
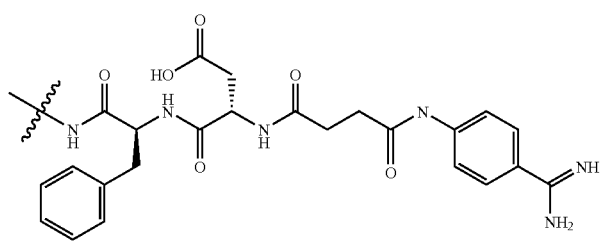
X:
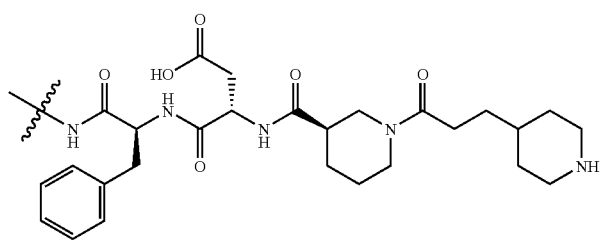
XI:
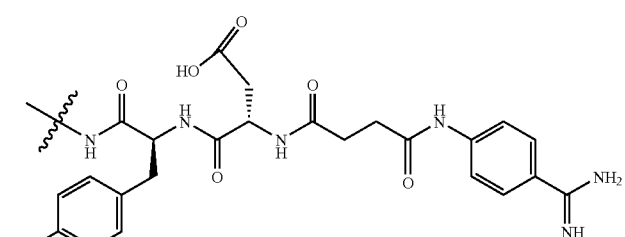
XII:
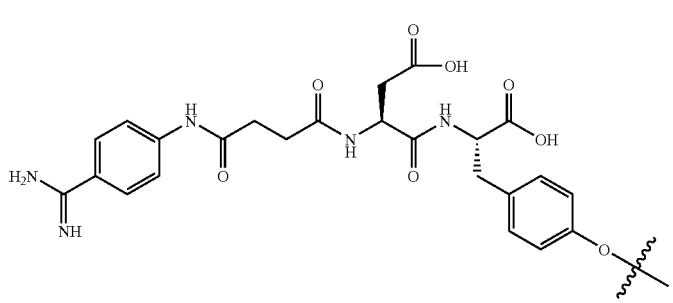
XIII:
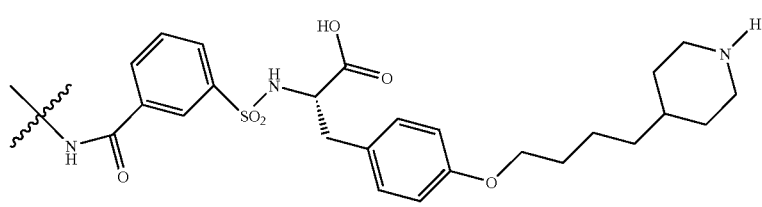

-continued
XV:
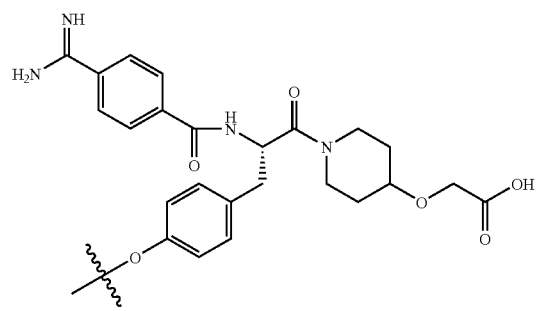
Analogously can be prepared, XVI:
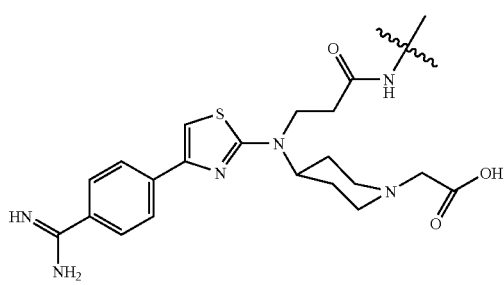
Scheme 9. Synthesis of XIV
63 + 52 ⟶
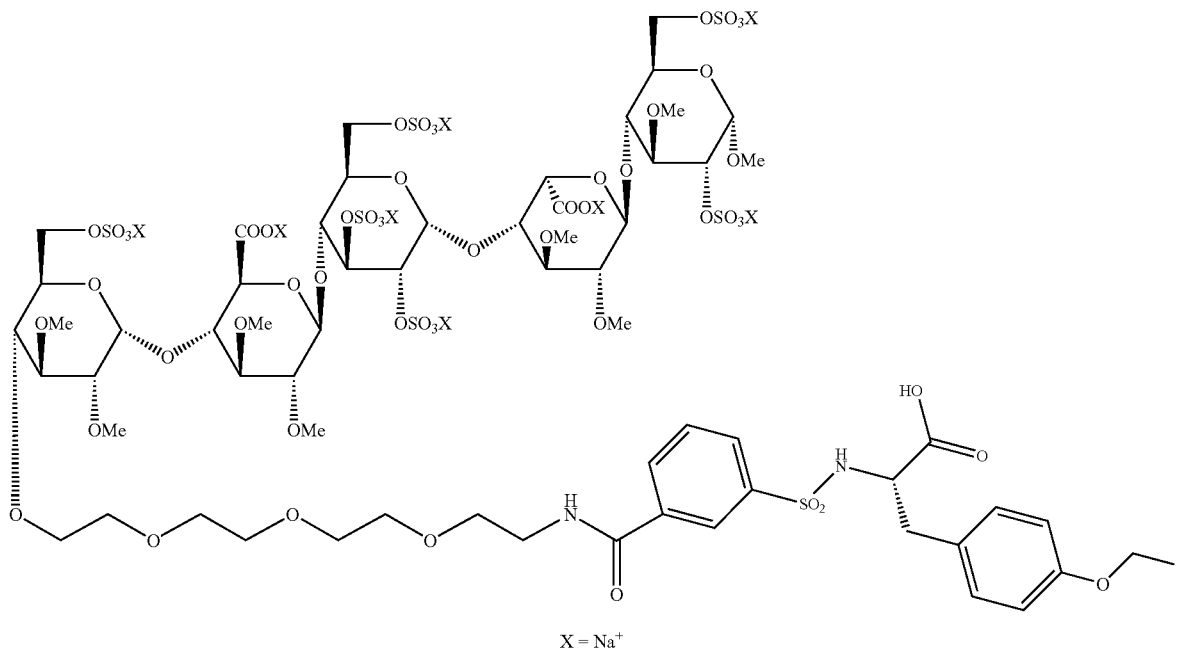
X = Na⁺
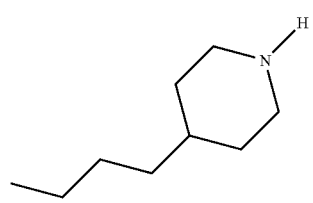

-continued
Scheme 10. Reference compounds.
XVII
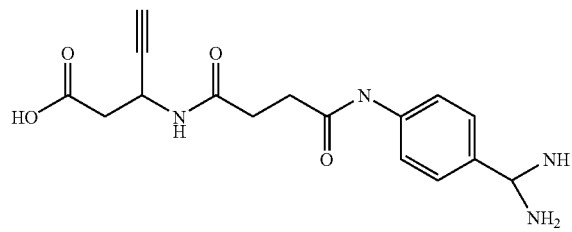
XVIII
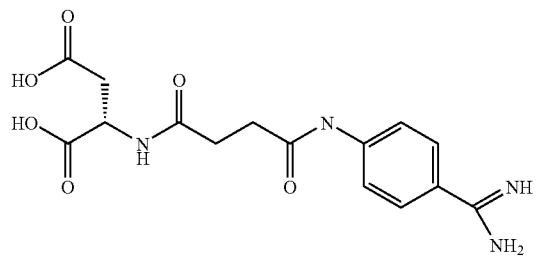
XIX
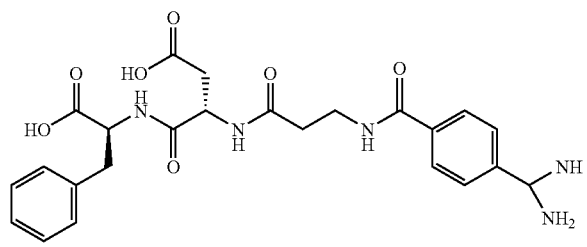
XX
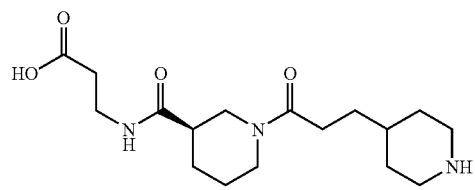
XXI
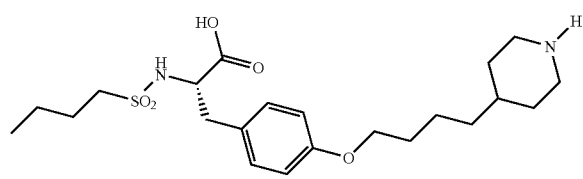
XXII
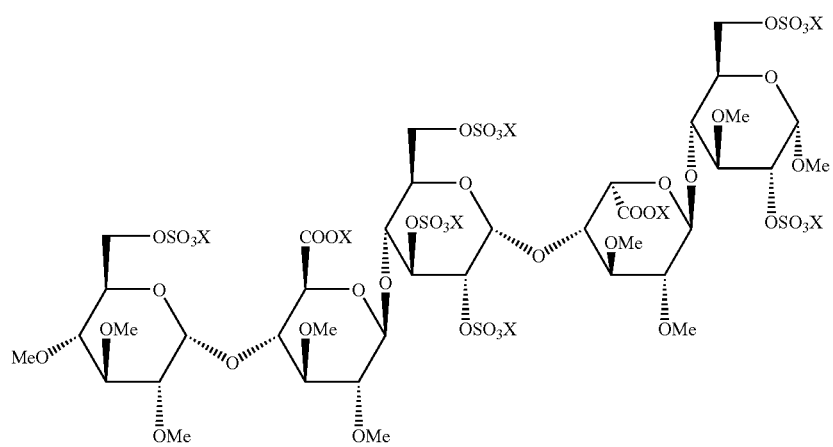
X = Na⁺

Pharmacological Data

I.a. In vitro Test for Inhibition of Human Platelet Aggregation Induced by ADP

Introduction:

Addition of adenosine diphosphate (ADP) to human platelet rich plasma (PRP) in vitro induces platelet aggregation. This aggregation can be assessed by measuring the optical density (OD) of the PRP. The in vitro test described here was used to determine the inhibitory activity of a test compound on the ADP-induced aggregation of human platelets. A micro plate reader is used to measure the activity of several compounds simultaneously.

Test medium: Platelets from healthy human volunteers who have not taken any drug during the preceding 10 days.

Ref. compound: In this assay, tirofiban (AGGRASTAT® (MSD) purchased as 0.25 mg/mL concentrate for i.v. infusion) inhibits human platelet aggregation induced by 5 μM ADP by 50% at a concentration of 30-60 nM ($IC_{50}$).

Vehicle: Test compounds should preferably be dissolved in MQ $H_2O$ at a concentration of 1 mM. An alternative vehicle is 0.9% NaCl in MQ $H_2O$. The compound solution (either in MQ $H_2O$ or 0.9% NaCl in MQ $H_2O$) is further diluted in 0.9% NaCl in MQ $H_2O$.

Technique:

Reagents
1. Platelet rich plasma (PRP):
   Free-flowing blood (at least 100 mL) is taken from a healthy volunteer and collected in 0.1 volume 3.8% sodium citrate. $2H_2O$ in distilled $H_2O$ (w/v). The final concentration is 0.38% sodium citrate.
   The citrated blood is centrifuged at 1,600 N/kg (160 g) at RT. After 15 min, centrifugation is discontinued with the brake turned off and the supernatant (=PRP) is collected.
2. ADP (Kordia/Chrono-par # 384). Before use, a solution of 50 μM in 0.9% NaCl is prepared.

Equipment
1. Sysmex blood cell counter model KX-21.
2. Labsystems iEMS reader MF with a 620 nm filter, an orbital shaker set at 1,000 rpm and a constant temperature of 37° C. Absorption is measured with the Labsystems iEMS program.
3. Blood collection system 600 mL with needle, art P4203 (NPBI).
4. 96 wells flat bottom micro plates (Greiner Labortechnik).

Procedure
The platelets in the supernatant (PRP) are counted using a Sysmex blood cell counter and the supernatant is diluted with PPP to obtain a PRP containing 400,000±50,000 plt/μL. PRP should stabilize at RT for at least 20 min but not longer than 3 h.

ADP-induced Aggregation
150 μL PRP is pipetted into a well of the micro plate. 30 μL test compound in a range of concentrations (7 concentrations per compound) or vehicle is added and the micro plate is placed in the Labsystems iEMS reader MF at 37° C. The optical density (OD620) is then measured at 620 nm. After shaking for 2 min in the reader (1,000 rpm), the OD is measured for the second time. This is to verify the stability of the platelets (absence of spontaneous platelet aggregation). Then, 20 μL of 50 μM ADP solution is added and the OD is kinetically measured every min for 14 min at 620 nm (FIG. 1). Between two measurements, the plate is shaking for 40 seconds at 1,000 rpm. Each test compound is investigated in at least 2 experiments using PRP from different volunteers. Usually, the highest final concentration of the test compound is between 1E-6 and 1E-7M and the compound concentrations are decreased by a factor 2 until a platelet aggregation inhibition of less than 25% is obtained.

Evaluation of Response ADP-Induced Aggregation
The mean OD at each compound concentration (including vehicle) is calculated at t=0 min and t=10 min. The percentage inhibition at each concentration is calculated using the formula:

$$100\% - \frac{(ODcompound \text{ at } t = 0 \text{ min} - ODcompound \text{ at } t = 10 \text{ min})}{(ODvehicle \text{ at } t = 0 \text{ min} - ODvehicle \text{ at } t = 10 \text{ min})} \times 100\%$$

The $IC_{50}$ of the test compound is the concentration of the test compound at which the ADP-induced platelet aggregation is reduced by 50%. For this, the percentage inhibition values are plotted against compound concentration. Then, $IC_{50}$, nH (Hill slope) and efficacy of the test compound is calculated using Graphpad Prism 3.0 (with variable slope).

Quantities required: 2 mg.

Reference: Salmon, D. M. (1996) Thrombosis Research 84, 213-216.

TABLE 1

Inhibition of ADP-induced (5 μM) human platelet aggregation ($IC_{50}$)

| Compound | MW | $IC_{50}$ in μM, mean | n[a] | Comparative sample |
|---|---|---|---|---|
| I | 786 | 0.61 | 1[b] | * |
| II | 2512 | 1.56 | 2[b] | |
| III | 639 | 0.38 | 1[b] | * |
| IV | 786 | 0.35 | 2[b] | * |
| V | 2512 | 0.69 | 6[b] | |
| VI | 383 | 22.58 | 2[b] | * |
| VII | 672 | 0.38 | 4[b] | * |
| VIII | 2398 | 2.30 | 2[b] | |
| IX | 819 | 1.18 | 2[b] | * |
| X | 2545 | 1.45 | 2[b] | |
| XII | 2530 | 0.47 | 3 | |
| XIII | 2520 | 0.10 | 3 | |
| XIV | 2287 | 0.63 | 2 | |
| XVII | 386 | 0.11 | 6[b] | * |
| XVIII | 350 | 2.01 | 2[b] | * |
| XIX | 497 | 0.08 | 2[b] | * |
| XX | 339 | 0.31 | 4[b] | * |
| XXI | 436 | 0.05 | 15 | * |

[a]n = number of experiments;
[b]Platelet aggregation was measured using a Chronolog aggregometer as described by Caron et al., (2002) J. Cardiovasc. Pharmacol. 40, 296-306.

I.b. In vitro Test for Inhibition of Human Platelet Aggregation Induced by TRAP

Introduction: Addition of trombin receptor agonist peptide (TRAP) to washed human platelets (WPL) in vitro induces platelet aggregation. This aggregation can be determined by measuring the optical density of the WPL. The in vitro test described here is used to analyze the activity of a test compound to inhibit TRAP-induced aggregation of human platelets. A micro plate reader is used to measure the activity of several compounds simultaneously.

Test medium: Platelets from healthy human volunteers who have not taken any drug during the preceding 10 days.

Ref. compound: In this assay, tirofiban (AGGRASTAT® (MSD)) purchased as 0.25 mg/mL concentrate for i.v. infusion) inhibits the human platelet aggregation induced by 5 µM TRAP by 50% at a final concentration of 30-60 nM (IC$_{50}$).

Vehicle: Test compounds should preferably be dissolved in MQ H$_2$O at a concentration of 1 mM. An alternative vehicle is 0.9% NaCl in MQ H$_2$O. The compound solution (either in MQ H$_2$O or 0.9% NaCl in MQ H$_2$O) is further diluted in 0.9% NaCl in MQ H$_2$O.

Technique:

Reagents

1. Platelet rich plasma (PRP):

Free-flowing blood (at least 100 mL) is taken from a healthy volunteer and collected in 0.1 volume 3.8% sodium citrate. 2H$_2$O in MQ H$_2$O (w/v). The final concentration is 0.38% sodium citrate. The citrated blood is centrifuged at 1,600 N/kg (160 g) in Hettich Rotanta/AP centrifuge (750 rpm) at RT. After 15 min, centrifugation is discontinued with the brake turned off and the supernatant (=PRP) is collected.

2. Washed platelets (WPL):

After adding freshly made 1 µL PGI$_2$ solution per ml PRP, the suspension is centrifuged at 13,500 N/kg (1,350 g) for 10 min in a Hettich Rotanta/AP centrifuge (i.e., 2,800 rpm) at RT. After gentle resuspension of the pellet in the same volume of fresh Watson buffer containing 5 ng/mL PGI$_2$, the suspension is centrifuged at 1,350 g (2,800 rpm) for 10 min at RT again. The final platelet pellet is resuspended in Watson buffer to give approx. 400,000±50,000 platelets/mL.

3. Watson buffer:

134 mM NaCl, 2.9 mM KCl, 12 mM NaHCO$_3$, 0.34 mM Na$_2$HPO$_4$.2H$_2$O, 1 mM MgCl$_2$.6H$_2$O, 5 mM Glucose and 5 mM HEPES in MQ H$_2$O. The pH is adjusted to 7.4 with 1 M NaOH.

4. Prostaglandin I$_2$ (Sigma, P6188 powder):

The PGI2 stock solution of 1 mg/mL in 1 M KOH is stored in aliquots of 100 µL at −20° C. Immediately before use, a solution of 5 µg/mL in ice-cold 0.9% NaCl in MQ H$_2$O is prepared.

5. Human Fibrinogen (Kordia/ERL, art nr: FIB 2 powder):

0.5 g fibrinogen powder is dissolved in 50 mL MQ H$_2$O under vacuum. This stock solution is stored in aliquots of 1 mL at −20° C. Before use, a solution of 0.5 mg/mL in saline is prepared.

6. TRAP

Before use, a solution of 50 µM TRAP in 0.9% NaCl in MQ H$_2$O is prepared. For each test, a fresh solution is made.

Equipment

1. Sysmex cell counter model KX-21
2. Labsystems iEMS reader MF with a 405 nm filter, an orbital shaker set at 1,000 rpm and a constant temperature of 37° C. Absorptions are measured with the Labsystems iEMS program.
3. Blood collection system 600 mL with needle, art nr P4203 (NPBI)
4. 96 wells micro plates (Greiner Labortechnik) flat-bottom Procedure: The WPL concentration is counted in a Sysmex blood cell counter and the suspension is diluted with Watson buffer to obtain a concentration of 400,000±50,000 plt/µL. Before use, WPL is allowed to stabilize at room temperature for at least 20 min but not longer than 3-4 hours.

TRAP-induced aggregation: 150 µL WPL is pipetted into a well of a micro plate. 15 µL test compound or vehicle and 15 µL fibrinogen solution is added and the micro plate is placed in the micro plate reader at 37° C. Then, the optical density (OD) is measured at 405 nm and after shaking for 2 min in the reader, the OD405 is measured again to verify the stability of the platelets (absence of spontaneous platelet aggregation). 20 µL of 50 µM TRAP is added and the OD405 is kinetically measured every min for 14 min at 405 nm. Between two measurements, the plate is shaking for 40 seconds at 1,000 rpm (FIG. 1). For determination of the IC$_{50}$ of a test compound, each test compound is investigated in at least 2 experiments using WPL from different volunteers. The usual starting concentration of the compound is between 1E-6M and 1E-7M in the incubation medium and the compound concentration is decreased by a factor 2 until a platelet aggregation inhibition of less than 25% is obtained.

Evaluation of response: The mean OD of each concentration (including vehicle) is calculated at t=0 min and t=10 min. The percentage inhibition at each concentration is calculated using the formula:

$$100\% - \frac{(ODcompound \text{ at } t = 0 \text{ min} - ODcompound \text{ at } t = 10 \text{ min})}{(ODvehicle \text{ at } t = 0 \text{ min} - ODvehicle \text{ at } t = 10 \text{ min})} \times 100\%$$

The concentrations of the compound are plotted against the percentage inhibition. The IC$_{50}$, nH (Hill slope) and efficacy of the test compound are calculated using Graphpad Prism 3.0 (with variable slope). The IC$_{50}$ of the test compound is the concentration at which the TRAP-induced platelet aggregation is reduced by 50%.

Quantities required: 2 mg.

Reference: Salmon D. M. (1996) Thrombosis Research 84, 213-216.

TABLE 2

Inhibition of TRAP (5 µM)-induced human platelet aggregation (IC$_{50}$)

| Compound | MW | IC$_{50}$ in µM, mean | n[a] | Comparative sample |
|---|---|---|---|---|
| I | 786 | 0.22 | 2[b] | * |
| II | 2512 | 0.31 | 2[b] | |
| III | 639 | 0.25 | 2[b] | * |
| IV | 786 | 0.12 | 2[b] | * |
| V | 2512 | 0.20 | 7[b] | |
| VI | 383 | 6.29 | 2[b] | * |
| VII | 672 | 0.27 | 5[b] | * |
| VIII | 2398 | 0.66 | 3[b] | |
| IX | 819 | — | — | * |
| X | 2545 | 0.76 | 3[b] | |
| XII | 2530 | 0.11 | 1 | |
| XIII | 2520 | 0.08 | 1 | |
| XIV | 2287 | 0.08 | 1 | |
| XVII | 386 | 0.10 | 4[b] | * |
| XVIII | 350 | 1.19 | 2[b] | * |
| XIX | 497 | 0.10 | 2[b] | * |
| XX | 339 | 0.38 | 2[b] | * |
| XXI | 436 | 0.05 | 8 | * |

[a]n = number of experiments;
[b]Platelet aggregation was measured using a Chronolog aggregometer as described by Caron et al., (2002) J. Cardiovasc. Pharmacol., 40, 296-306.

II. Determination of Anti-Factor Xa Activity in Buffer (Microtiter Plate Method)

Introduction:

Activated factor X (X$_a$) is a factor in the coagulation cascade; its activity is slightly inhibited by antithrombin III (AT-III). Anticoagulants can inhibit $X_a$ directly or, like heparin, by potentiating the inhibitory activity of AT-III. Anti-$X_a$ activity can be assessed by determination of the rate of hydrolysis of the chromogenic substrate S-2222 in the presence of AT-III. This assay is used to determine anti-$X_a$ activity of heparinoid preparations in Kabi buffer.

Test medium: Kabi buffer.

Ref. compound: International standard heparin (11.4 anti-$X_a$ U/mg).

Technique:

Reagents

1. Kabi buffer

Composition of the buffer: NaCl 10.17 g (174 mmol); edetate disodium dihydrate 3.26 g (9.6 mmol); tromethamine (Tris) 6.11 g (50.4 mmol); made up to 1 L with ultrapure $H_2O$ *. The pH of the solution is adjusted to 7.4 with hydrochloric acid (0.10 mol/L)

* For all aq. solutions ultrapure $H_2O$ (Milli-Q quality) is used.

2. $X_a$ solution

Bovine factor $X_a$ (Kabi Diagnostica, Stockholm, Sweden) is dissolved in Kabi buffer to give a solution containing 1.5 U/mL (0.75 nKat/mL).

3. S-2222 solution

S-2222 (Kabi Diagnostica) is dissolved in ultrapure $H_2O$ to give a solution containing 0.375 mg/mL (0.5 mmol/L).

4. AT-III solution

Human AT-III (Kabi Diagnostica) is dissolved in Kabi buffer to give a solution containing 0.25 U/mL. A fresh solution has to be prepared daily.

5. Standard solution of the calibration sample

Standard heparin is dissolved in Kabi buffer to give a standard solution containing approx. 0.25 anti-$X_a$ U/mL.

Procedure:

Preparation of Test Samples

Each preparation is dissolved in ultrapure $H_2O$ and diluted with Kabi buffer to the required concentrations in the range of 0.02-0.2 anti-$X_a$ U/mL Determination of $X_a$ Activity Each test sample (0.05 mL) is pipetted into a well of a microtiter plate at RT. AT-III solution (0.05 mL) is added to each sample and the plate is shaken using a Vari-shaker.

An aliquot of $X_a$ solution (0.05 mL) is pipetted into each well 10 min following addition of AT-III solution and the plate is shaken again. Exactly 2 min following addition of $X_a$ solution, 0.1 mL S-2222 solution is pipetted into each well and the plate is shaken again. For all additions a 12-channel pipette is used.

The remaining amount of $X_a$ catalyses the hydrolysis of S-2222, the rate of which is measured photometrically following incubation periods of 2 and 22 min respectively at RT. The absorbance of each sample is measured at 405 nm using a Reader Microelisa, model 310C (Organon Teknika, Oss, The Netherlands) and the increase in absorbance ($\Delta OD$) is calculated. Each test sample is determined in duplicate. With every 10 samples, a blank (0.05 mL Kabi buffer) is included.

Calibration Curve

From an aliquot of the standard solution of the calibration sample a range of dilutions is made (dilution factor 1,3 for heparin samples). The resulting standard samples (approx. 15 samples) should contain between 0.01-0.25 anti-$X_a$ U/mL. Within each run, 0.05 mL of each standard sample is tested at least 3 times as described under Determination of $X_a$ activity. A calibration curve is obtained by fitting a straight line to $$\log \frac{\text{mean } \Delta OD \text{ (blank)} - \text{mean } \Delta OD \text{ (standard sample)}}{\text{mean } \Delta OD \text{ (standard sample)}}$$

against log anti-Xa U/mL values, using the method of least squares.

Evaluation of Responses:

For each sample the mean anti-$X_a$ activity in U/mL is determined using the calibration curve. For comparison, the anti-$X_a$ activity data of the free pentasaccharide XXII, the "parent" of the oligosaccharide part of the conjugates, are also presented.

TABLE 3

Anti-Xa activities of pentasaccharide conjugates

| Compound | Mw | U/mg | U/nmol | Comparative sample |
|---|---|---|---|---|
| II | 2512 | 618 ± 32 | 1.55 | |
| V | 2512 | 565 ± 32 | 1.42 | |
| VIII | 2398 | 605 ± 43 | 1.45 | |
| X | 2545 | 545 ± 38 | 1.39 | |
| XII | 2530 | 619 ± 157 | 1.57 | |
| XIII | 2520 | 671 ± 119 | 1.69 | |
| XIV | 2287 | 735 ± 107 | 1.68 | |
| XXII | 1639 | 775 ± 23 | 1.27 | * |

Pharmacokinetics

Guinea pigs (DH) were administered 0.5 µmol/kg (i.v.) of anticoagulant. The half-life of the pentasaccharide XXII, the "parent" of the oligosaccharide part of the conjugates, and conjugate VIII were indirectly assigned by ex-vivo determination of plasma anti-Xa activity at specific time-intervals as described above. The half-lives of the reference GPIIb/IIIa antagonists XVII, XIX and XX (see Scheme 10) were determined by measuring the plasma concentration at specific time-intervals using LC-MS/MS.

CONCLUSION

The half life of the conjugate compound VIII of this invention is significantly prolonged when compared to the reference GpIIb/IIIa antagonists.

What is claimed is:

1. A compound of the formula A oligosaccharide-spacer-GpIIb/IIIa antagonist                    (A), wherein the compound is selected from the following compounds:

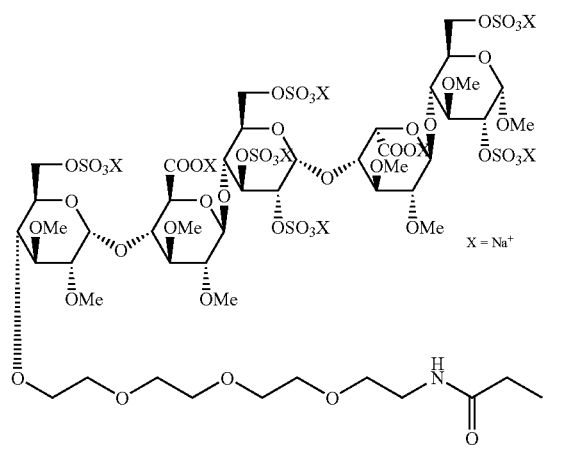
GPIIb/IIIa =
II:
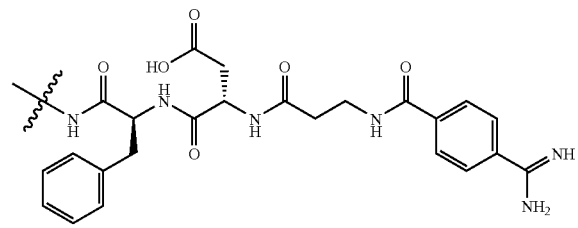
VIII:
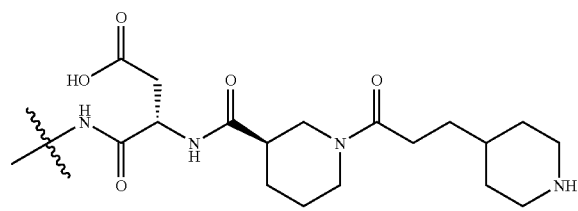
V:
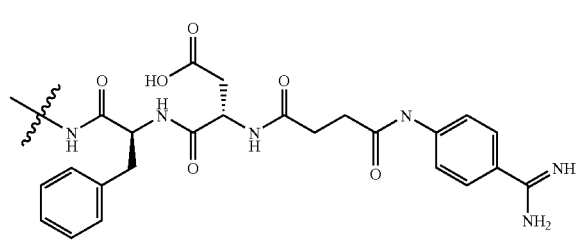
X:
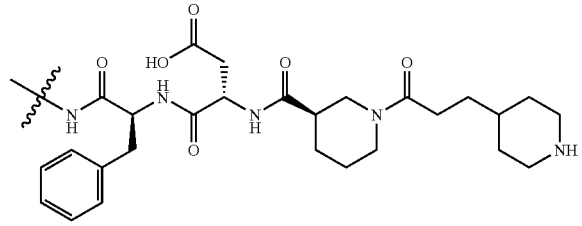
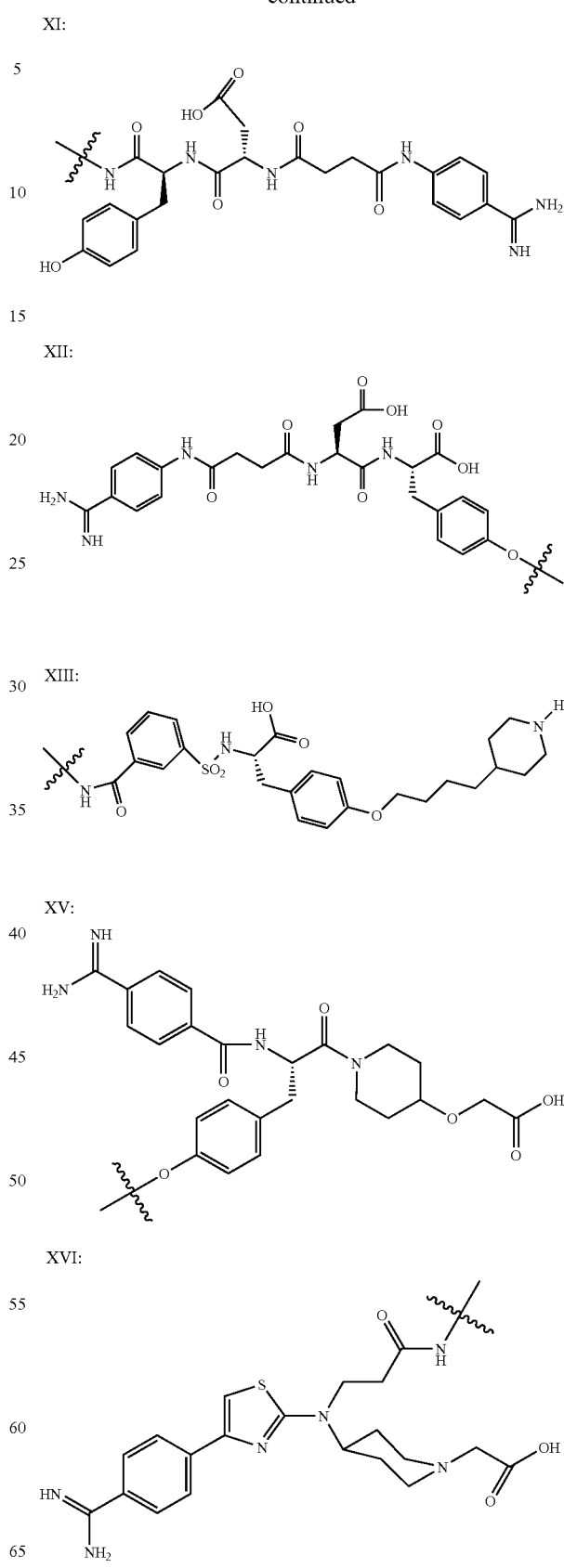

and

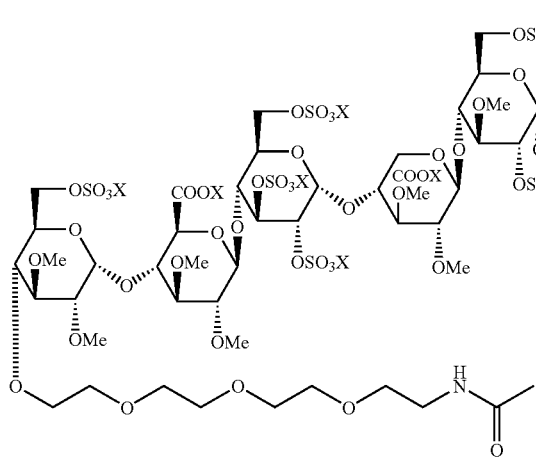

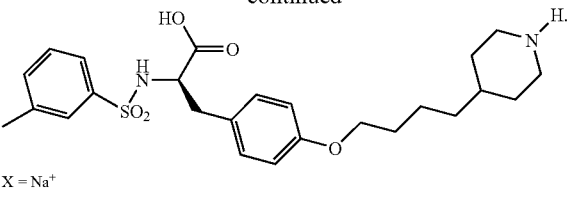

X = Na⁺

2. A pharmaceutical composition comprising a compound of claim 1 and pharmaceutically suitable auxiliaries.

3. A method of treating a thrombotic disorder, comprising: administering to a patient in need thereof a therapeutically effective amount of a compound according to claim 1.

4. The method of claim 3, wherein the thrombotic disorder is selected from: acute myocardial infarction, ischemia and stroke.

* * * * *